(12) United States Patent
Verdine et al.

(10) Patent No.: US 9,585,964 B2
(45) Date of Patent: Mar. 7, 2017

(54) LIVER TARGETED CONJUGATES

(71) Applicant: President and Fellows of Harvard College, Cambridge, MA (US)

(72) Inventors: Gregory L. Verdine, Newton, MA (US); Yoshihiko Norimine, Tsukuba (JP); Lourdes Gude-Rodriguez, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 552 days.

(21) Appl. No.: 13/869,917

(22) Filed: Apr. 24, 2013

(65) Prior Publication Data

US 2013/0245101 A1  Sep. 19, 2013

Related U.S. Application Data

(63) Continuation of application No. 11/994,868, filed as application No. PCT/US2006/026147 on Jul. 5, 2006, now abandoned.

(60) Provisional application No. 60/697,015, filed on Jul. 5, 2005.

(51) Int. Cl.

| A61K 31/21 | (2006.01) |
|---|---|
| A61K 47/48 | (2006.01) |
| A61K 31/22 | (2006.01) |
| A61K 31/405 | (2006.01) |
| C07D 209/28 | (2006.01) |
| C07D 309/30 | (2006.01) |
| C07D 405/12 | (2006.01) |
| C07D 405/14 | (2006.01) |

(52) U.S. Cl.
CPC ........ *A61K 47/48061* (2013.01); *A61K 31/22* (2013.01); *A61K 31/405* (2013.01); *A61K 47/481* (2013.01); *A61K 47/48092* (2013.01); *A61K 47/48107* (2013.01); *C07D 209/28* (2013.01); *C07D 309/30* (2013.01); *C07D 405/12* (2013.01); *C07D 405/14* (2013.01)

(58) Field of Classification Search
CPC .................................................... A61K 31/21
See application file for complete search history.

(56) References Cited

U.S. PATENT DOCUMENTS

| 4,661,483 A | 4/1987 | Hoffman et al. |
|---|---|---|
| 5,286,746 A | 2/1994 | Poss |
| 5,412,120 A | 5/1995 | Fischer et al. |
| 6,207,700 B1 | 3/2001 | Kalgutkar et al. |
| 6,548,532 B2 | 4/2003 | Dalko et al. |

(Continued)

FOREIGN PATENT DOCUMENTS

| DE | 202004009305 | 9/2004 |
|---|---|---|
| EP | 0 245 003 | 11/1987 |

(Continued)

OTHER PUBLICATIONS

International Search Report and Written Opinion for PCT/US2006/026147, mailed Jan. 29, 2007.

(Continued)

*Primary Examiner* — Benjamin Packard
(74) *Attorney, Agent, or Firm* — Wolf, Greenfield & Sacks, P.C.

(57) ABSTRACT

Therapeutic conjugates containing a statin or a modified statin (collectively "statin") linked to a therapeutic agent (also referred to as a drug herein) are targeted to the liver by the statin or modified statin and thereby deliver the therapeutic agent to liver cells.

16 Claims, 8 Drawing Sheets

| Treatment | Route | Dose | % Reduction of ALT | % Reduction of AST |
|---|---|---|---|---|
| Ind-S | IP | 5 μmol/kg x 3 | 21 | (34) |
| Ind-S | IP | 1 μmol/kg x 3 | -20 | -21 |
| Ind-S | IP | 0.5 μmol/kg x 3 | -7 | -23 |
| Lovastatin | IP | 30 mg/kg x 3 | -17 | -38 |
| Indomethacin | IP | 5 μmol/kg x 3 | -39 | -73 |
| Silymarin | PO | 300 mg/kg x 3 | (50) | (42) |

(56) References Cited

U.S. PATENT DOCUMENTS

| | | |
|---|---|---|
| 2002/0077317 A1 | 6/2002 | Das |
| 2003/0049314 A1 | 3/2003 | Liang et al. |
| 2003/0149010 A1 | 8/2003 | Keller et al. |
| 2003/0232033 A1 | 12/2003 | Cantrell |
| 2009/0162316 A1 | 6/2009 | Verdine et al. |

FOREIGN PATENT DOCUMENTS

| | | |
|---|---|---|
| WO | WO 00/45817 | 8/2000 |
| WO | WO 02/28270 | 4/2002 |
| WO | WO 2004/004778 | 1/2004 |

OTHER PUBLICATIONS

International Preliminary Report on Patentability for PCT/US2006/026147, issued Jan. 9, 2008.

Erkelens, "Combination Drug Therapy with HMG CoA Reductase Inhibitors and Bile Acid Sequestrants for Hypercholesteremia," Cardiology, 77:33-38 (1990).

| Treatment | Route | Dose | % Reduction of ALT | % Reduction of AST |
|---|---|---|---|---|
| Ind-S | IP | 5 µmol/kg x 3 | 21 | (34) |
| Ind-S | IP | 1 µmol/kg x 3 | -20 | -21 |
| Ind-S | IP | 0.5 µmol/kg x 3 | -7 | -23 |
| Lovastatin | IP | 30 mg/kg x 3 | -17 | -38 |
| Indomethacin | IP | 5 µmol/kg x 3 | -39 | -73 |
| Silymarin | PO | 300 mg/kg x 3 | (50) | (42) |

FIGURE 1

| COMPOUND CODE | PT NUMBER | BATCH* | SPE | n= | CONC. | % | ↑ % INHIBITION<br>-100  -50   0   50  100<br>↓    ↓    ↓   ↓   ↓ | IC₅₀ |
|---|---|---|---|---|---|---|---|---|
| 124000 HMG-CoA Reductase | | | | | | | | |
| IN-s | 1043315 | 108086 rat | | 2 | 10 µM | 99 | | 0.0292 µM |
| IN-s | 1043315 | 108086 rat | | 2 | 0.1 µM | 70 | | 0.0292 µM |
|  |  |  |  | 2 | 1 nM | -4 | | |
| Su-s | 1043316 | 108086 rat | | 2 | 10 µM | 100 | | 0.0357 µM |
|  |  |  |  | 2 | 0.1 µM | 69 | | |
|  |  |  |  | 2 | 1 nM | -4 | | |
| Na-s | 1043317 | 108086 rat | | 2 | 10 µM | 95 | | 0.117 µM |
|  |  |  |  | 2 | 0.1 µM | 47 | | |
|  |  |  |  | 2 | 1 nM | -4 | | |
| Ib-s | 1043318 | 108086 rat | | 2 | 10 µM | 100 | | 0.0832 µM |
|  |  |  |  | 2 | 0.1 µM | 52 | | |
|  |  |  |  | 2 | 1 nM | -4 | | |
| Nia5-s | 1043321 | 108086 rat | | 2 | 10 µM | 97 | | 0.11 µM |
|  |  |  |  | 2 | 0.1 µM | 45 | | |
|  |  |  |  | 2 | 1 nM | 15 | | |
| Nia6-s | 1043322 | 108086 rat | | 2 | 10 µM | 96 | | 0.19 µM |
|  |  |  |  | 2 | 0.1 µM | 38 | | |
|  |  |  |  | 2 | 1 nM | 9 | | |
| Ol-s | 1043323 | 108086 rat | | 2 | 10 µM | 99 | | 2.03 nM |
|  |  |  |  | 2 | 0.1 µM | 100 | | |
|  |  |  |  | 2 | 1 nM | 27 | | |

FIGURE 2

LIVER TARGETED CONJUGATES

BACKGROUND

Statins, which are HMGCoA reductase inhibitors, are widely prescribed for lowering plasma cholesterol. Statins accumulate in the liver, and this is due at least in part to the abundance of the statin target protein, HMGCoA reductase, in the liver.

SUMMARY

Therapeutic conjugates containing a statin or a modified statin (collectively "statin") linked to a therapeutic agent (also referred to as a drug herein) are disclosed. The therapeutic agent can be any therapeutic agent. In some cases the therapeutic agent is an anti-inflammatory agent (e.g., an NSAID) in other cases the therapeutic agent is a nucleic acid molecule. The conjugates are targeted to the liver by the statin or modified statin and thereby deliver the therapeutic agent to liver cells. Without being bound by any particular theory, it is thought that the statin portion of the conjugate is recognized by hepatocytes. This can allow increased local concentration of the conjugate in the liver. Thus, the conjugate can effectively reach various types of liver cells, including Kuppfer cells and vascular endothelial cells. Is some cases the conjugate is intracellularly processed, e.g., by enzymatic cleavage, to release the statin and the therapeutic agent which can act within the cell or diffuse to other cells. In some cases one or both of the therapeutic agent and the statin are active when conjugated, and in some cases one or both are active when the conjugate is enzymatically cleaved to release the therapeutic agent and the statin.

The therapeutic conjugates are bi-functional in that they provide both a statin, which allows the conjugate to be targeted to liver cells (and can inhibit HMGCoA reductase), and a second, therapeutic agent, for example, an anti-inflammatory agent. Because the statin or modified statin targets the conjugate to the liver, the second therapeutic agent can be administered at a lower dosage than would otherwise be efficacious. This allows administration of the second therapeutic agents at dosages that elicit fewer or less severe side-effects. Thus, under some circumstances, the therapeutic conjugates can be used to administer a therapeutic agent that was previously considered undesirable either generally or for treatment of particular conditions or disorders due to unacceptable toxicity in some or all patients.

In some cases, the therapeutic conjugate is processed in vivo, by an esterase, such that the therapeutic agent is released from the statin. In some cases the statin will have the ability to inhibit HMGCoA reductase before processing. In some cases the statin will not have the ability to inhibit HMGCoA reductase before processing, but will gain this ability upon processing. In some cases the statin will not have the ability to inhibit HMGCoA reductase before or after processing. In such cases the statin serves a targeting function, but not necessarily a therapeutic function.

Depending on the nature of the therapeutic agent linked to the statin, the conjugates are useful for treating liver disorders such as hepatocellular carcinoma, liver inflammation hepatitis (e.g., hepatitis A, B, C, D and E), and liver fibrosis. The conjugates are also useful for treating disorders in which liver inflammation or another liver dysfunction play a role, for example, diabetes.

The statin can be linked to the therapeutic agent through a linker, for example, a linker that is cleaved in a liver cell to release the statin and the therapeutic agent. The cleavage can occur at one or more bonds within the linker. The bonds between the statin and the second therapeutic agent, the statin and the linker (where a linker is present) and the therapeutic agent and the linker (where a linker is present) can be covalent. Suitable linkers include: an ester group, an amide group, a carbamate group, a carbonate group, a cycloketal group, a thioester group, a thioamide group, and a thiocarbamate group. In some cases the cleavage yields an unmodified therapeutic agent and a statin. In other cases one or both of the released therapeutic agent and the released statin are modified by the presence of additional atoms derived from the linker.

The statin can be, for example, simvastatin, fluvastatin, pravastatin, cerivastatin, lovastatin, or atorvastatin.

Suitable molecules include those having Formula I and Formula II, below:

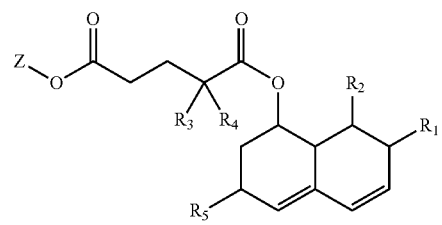

Formula I

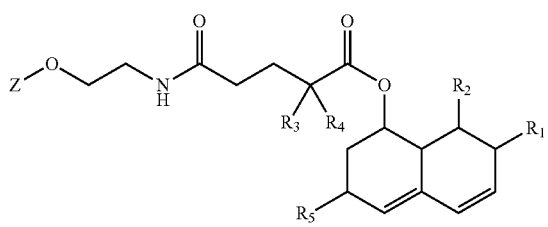

Formula II wherein Z is a therapeutic agent;

$R_3$ and $R_4$ are independently selected from —$CH_3$, —OH, H, a halogen, —$CH_2CH_3$ and cyclopropyl;

$R_1$ and $R_5$ are independently selected from —$CH_3$ and H;

$R_2$ is selected from:

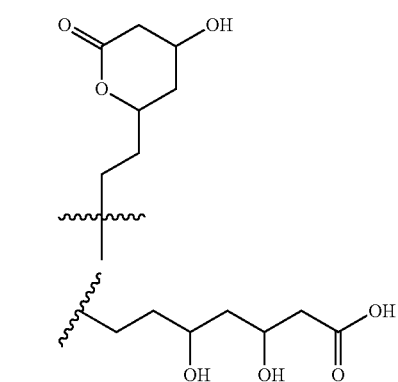

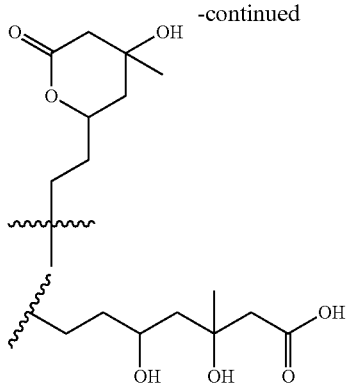

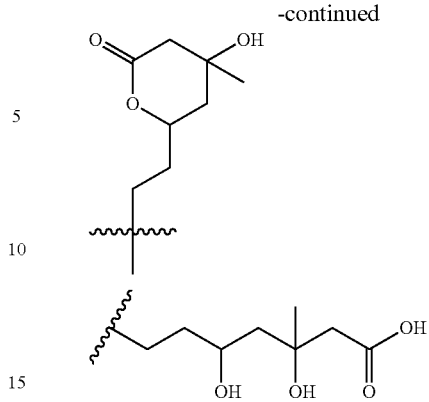

Among therapeutic agents that could be linked to the statin are: niacin, diclofenac, etoldolac, fenoprofen, floctafenine, flurbiprofen, ibuprofen, indoprofen, indomethacin, ketoprofen, ketorolac, lomoxicam, morazone, naproxen, perisoxal, pirprofen, pranoprofen, suprofen, suxibuzone, tropesin, ximoprofen, zaltoprofen, zileuton, zomepirac, salicylate, a steroid hormone and pharmaceutically acceptable salts, esters and prodrugs thereof. Additional therapeutic agents include peptides, proteins and nucleic acid molecules, for example, antisense molecules.

Described herein are compounds comprising an HMG-CoA reductase inhibitor and a linker suitable for covalent attachment of a selected compound. In various embodiments: the HMG-CoA reductase inhibitor is a statin (e.g., simvastatin, fluvastatin, pravastatin, cerivastatin, lovastatin, or atorvastatin); the compound has the formula:

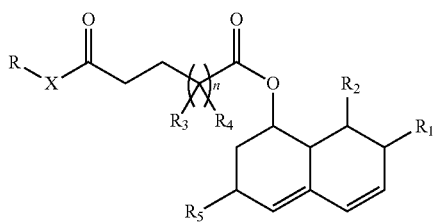

wherein R is: H, a $C_1$ to $C_6$ allyl, alkenyl or alkynl optionally substituted with one or more —OH or halogen; n is 1, 2, 3, 4, 5, or 6; X is S, O or N; $R_3$ and $R_4$ are independently selected from —$CH_3$, —OH, H, —$CH_2CH_3$, cyclopropyl and a halogen; $R_1$ and $R_5$ are independently selected from —$CH_3$ and H; and $R_2$ is selected from:

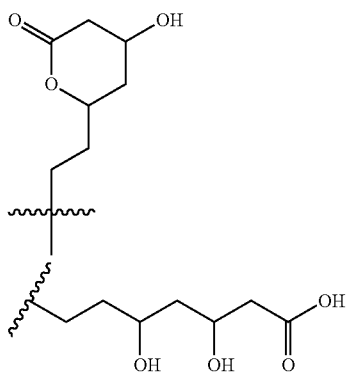

In various embodiments: n is 3; X is O and R is H or —$CH_2CH_2OH$; and the compound has the formula:

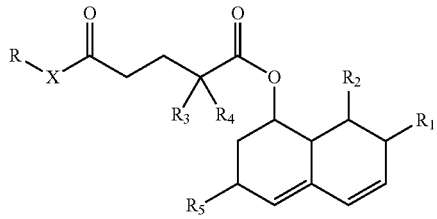

In certain embodiments both $R_3$ and $R_4$ are —$CH_3$ or $R_3$ is —$CH_3$ and $R_4$ is H.

Also described are compounds comprising a HMG-CoA reductase inhibitor covalently attached to a therapeutic agent through a linker. In various embodiments: the linker is an ester group, an amide group, a carbamate group, a carbonate group, a cycloketal group, a thioester group, a thioamide group, or a thiocarbamate group; the linker is cleaved in a liver cell; the HMG-CoA reductase inhibitor is a statin (e.g., simvastatin, fluvastatin, pravastatin, cerivastatin, lovastatin, or atorvastatin); the therapeutic agent is selected from the group consisting of: an angiotensin inhibitor, colchicine, a corticosteroid, an endothelin inhibitor, interferon-α, IL-10, interferon-β, pentoxifylline, phosphotidylcholine, a PPAR antagonist, S-adenosyl-methionine, and tocoherol; and the compound has the formula:

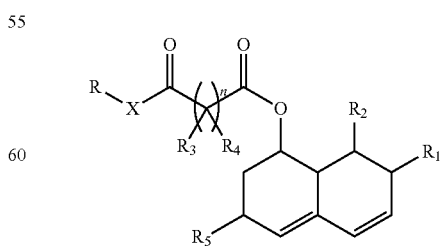

wherein R is a therapeutic agent; n is 1, 2, 3, 4, 5, or 6; X is S, O or N; $R_3$ and $R_4$ are independently selected from —CH₃, —OH, H, —CH₂CH₃, cyclopropyl and a halogen; R₁ and R₅ are independently selected from —CH₃ and H; and R₂ is selected from

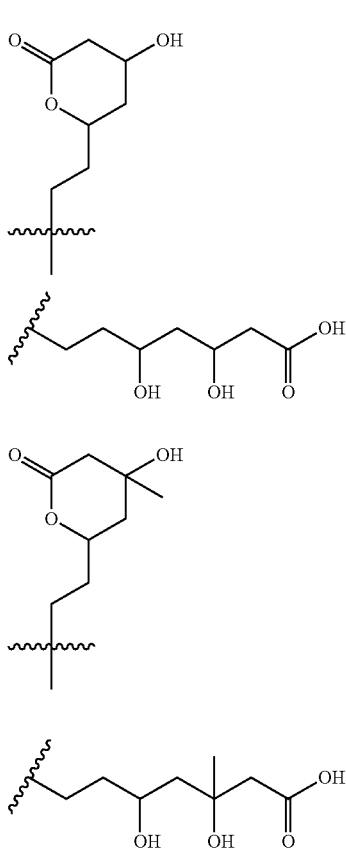

In some embodiments this compound has the structure:

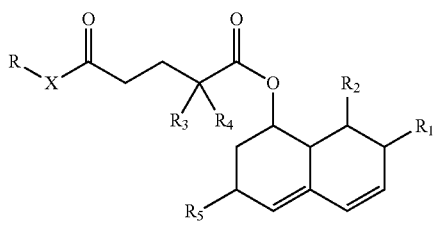

In various embodiments: R₁ is methyl; R₂ is

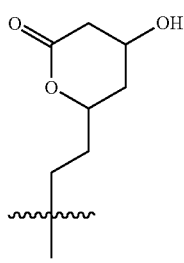 [SMILES: *CCC1CC(O)CC(=O)O1]

R₃ and R₄ are methyl; R₅ is methyl; X is N; R is an anti-inflammatory agent; and is

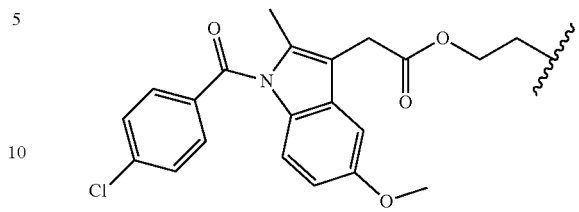

In some embodiments: the therapeutic agent is an anti-inflammatory agent; the therapeutic agent is selected from diclofenac, etoldolac, fenoprofen, floctafenine, flurbiprofen, ibuprofen, indoprofen, indomethacin, ketoprofen, ketorolac, lomoxicam, morazone, naproxen, perisoxal, pirprofen, pranoprofen, suprofen, suxibuzone, tropesin, ximoprofen, zaltoprofen, zileuton, zomepirac, salicylate, a steroid hormone and pharmaceutically acceptable salts, esters and prodrugs thereof; the therapeutic agent is a COX-2 inhibitor (e.g., a selective COX-2 inhibitor); the therapeutic agent is a chemotherapeutic agent; the therapeutic agent is an anti-viral agent; the therapeutic agent is an oligonucleotide; therapeutic agent is a nucleoside or nucleoside analogue; chemotherapeutic agent is 5FdU; chemotherapeutic agent is methotrexate; the chemotherapeutic agent is selected from: a bleomycin, capecitabine, carubicin, chlorozotocin, a chromomycin, cladribine, colchicine, cytarabine, daunorubicin, demecolcine, denopterin, docetaxel, doxyifluridine, doxorubicin, dromostanolone, edatrexate, enocitabine, epirubicin, epitiostanol, estramustine, etoposide, floxuridine, fludarabine, formestane, gemcitabine, irinotecan, lentinan, lonidamine, melengestrol, melphalan, menogaril, mitolactol, nogalamycin, nordihydroguaiaretic acid, an olivomycin, paclitaxel, pentostatin, pirarubicin, plicamycin, porfiromycin, prednimustine, puromycin, ranimustine, a ristocetin, temozolamide, teniposide, tomudex, topotecan, tubercidin, ubenimax, valrubicin, vinorelbine, vinblastine, vindesine, vinorelbine, and zorubicin and pharmaceutically acceptable salts, esters and prodrugs thereof; the therapeutic agent is an NFκB inhibitor; the therapeutic agent is a TGF-β inhibitor; the therapeutic agent is a PDGF inhibitor; the therapeutic agent is an inhibitor of an acute phase protein (e.g., the acute phase protein is IL-6 or TNF); the therapeutic agent is 20S,21 resibufogenin-3-formate; the therapeutic agent is an IKK-α, IKK-β, or a IKK-α/LKK-β inhibitor; the therapeutic agent is salicylate; and the therapeutic agent is 2-[(aminocarbonyl)amino]-5-(4-fluorophenyl)-3-thiophenecarboxamide.

Also described are compounds comprising a statin covalently bonded to a therapeutic agent.

Described herein are methods for targeting a therapeutic agent to the liver, the method comprising administering a compound comprising the therapeutic agent covalently linked to an HMG-CoA reductase inhibitor. In certain embodiments: the HMG-CoA reductase inhibitor is a statin; and the therapeutic agent is selected from niacin, cyclosporine, azothioprine, ursodeoxycholic acid, and ibuprofen.

Described herein is a method of treating a disorder of the liver (e.g., liver fibrosis and liver cirrhosis, non-alcoholic fatty liver diseases, non-alcoholic steatohepatitis, alcohol-induced liver disease, drug-induced liver disease, and primary biliary cirrhosis) comprising administering a compound described herein to a patient. Also described is a method for treating a disorder associated with inflammation of the liver, the method comprising administering a therapeutically effective amount a compound described herein. In various embodiments: the method further comprising administering a therapeutic agent that is not covalently linked to a statin or a statin not covalently linked to a therapeutic agent or both; the therapeutic agent is selected from ursodeoxycholic acid, azothioprine, cyclosporine and methotrexate. Also described are methods for: treating hepatitis comprising administering a therapeutically effective amount a compound described herein treating heptocellular carcinoma comprising administering a therapeutically effective amount of a compound described herein, and a method for treating type 2 diabetes comprising administering a therapeutically effective amount of a compound described herein.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a Table presenting the results of a study on the effect of various exemplary conjugates on $CCl_4$ induced liver damage in rats.

FIG. 2 is a Table presenting the results of a study on ability of various exemplary conjugates to inhibit HMGCoA reductase.

DETAILED DESCRIPTION

Figure 3:
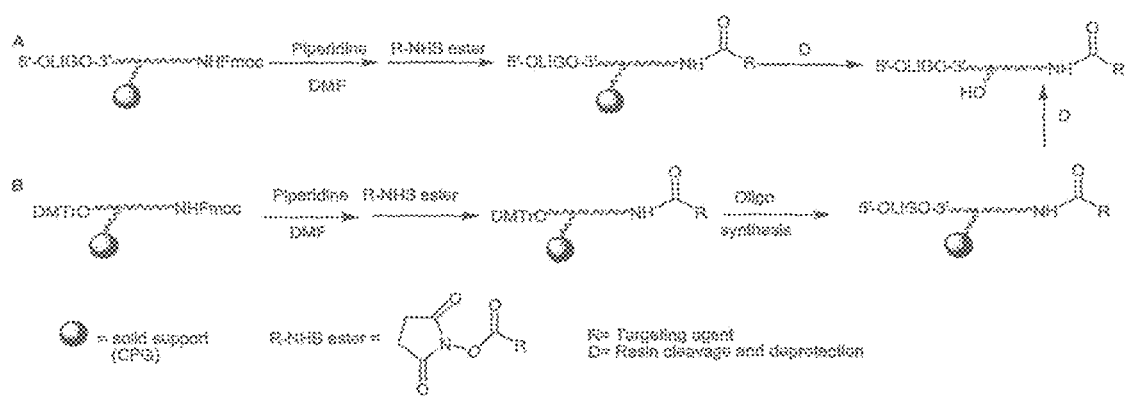
FIG. 3 is a schematic depiction of a method for linking the 3' end of a nucleotide or nucleic acid molecule to a statin or other targeting agent.
Figure 4:
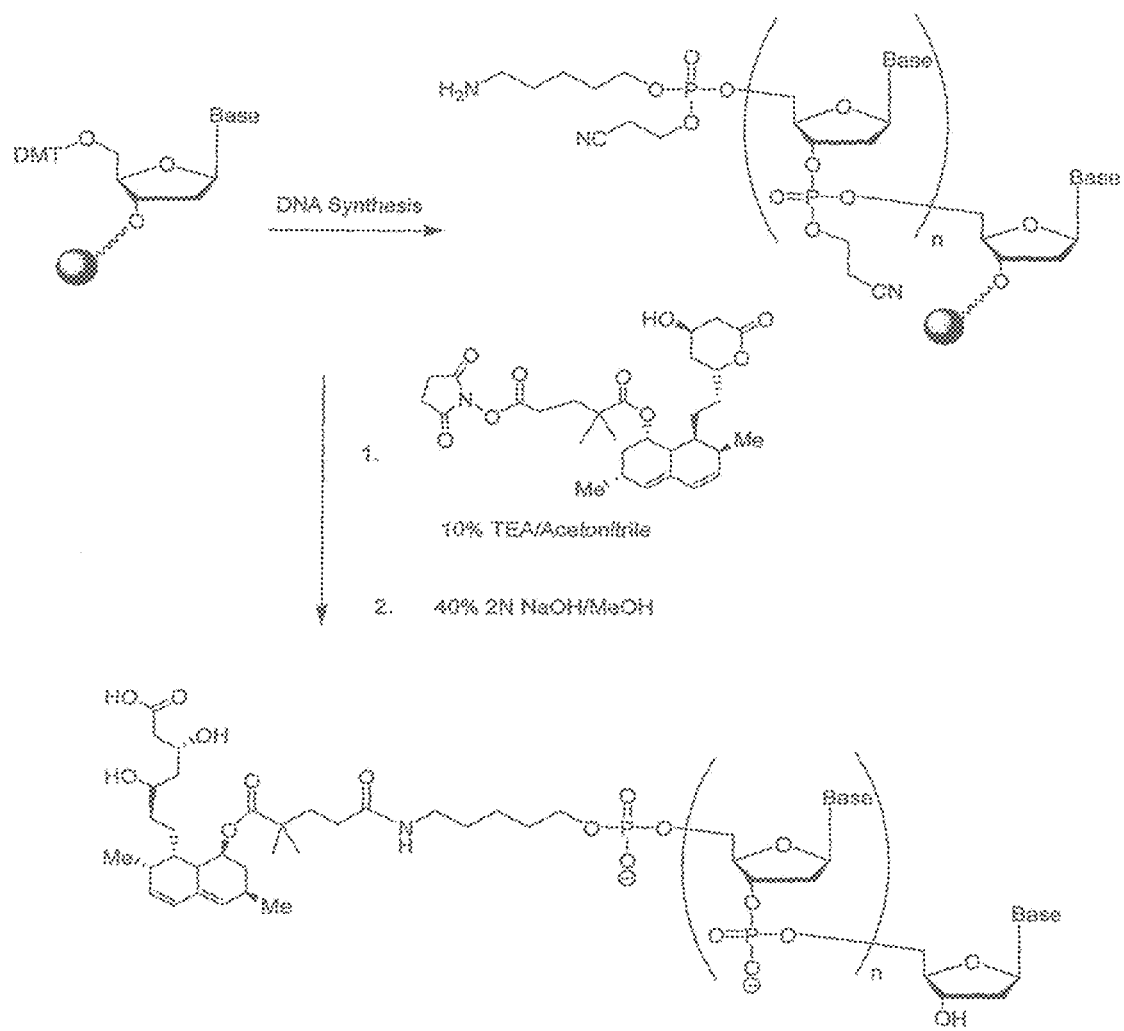
FIG. 4 is a schematic depiction of a method for linking the 5' end of a nucleotide or nucleic acid molecule to a statin.

A statin, a modified statin or a statin-like molecule can be used to target therapeutic agents to the liver. Suitable exemplary statins include: simvastatin, fluvastatin, pravastatin, cerivastatin, lovastatin, and atorvastatin.

Atorvastatin and related statins can be linked to one or two therapeutic agents indicated by R in the formula below, which depicts the open form of atorvastatin. Where two therapeutic agents are linked they can be the same or different.

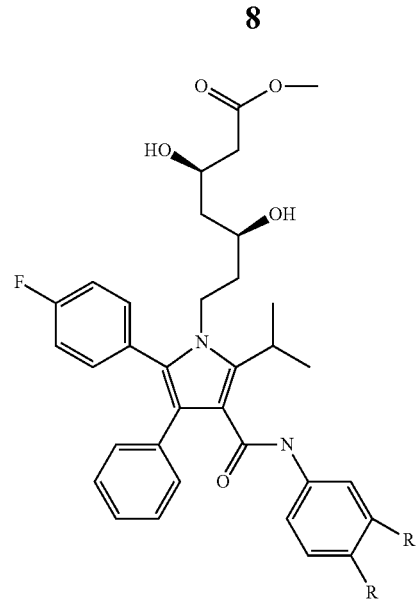

For example, a therapeutic agent R can be linked to atorvastatin in either of the configurations depicted below.

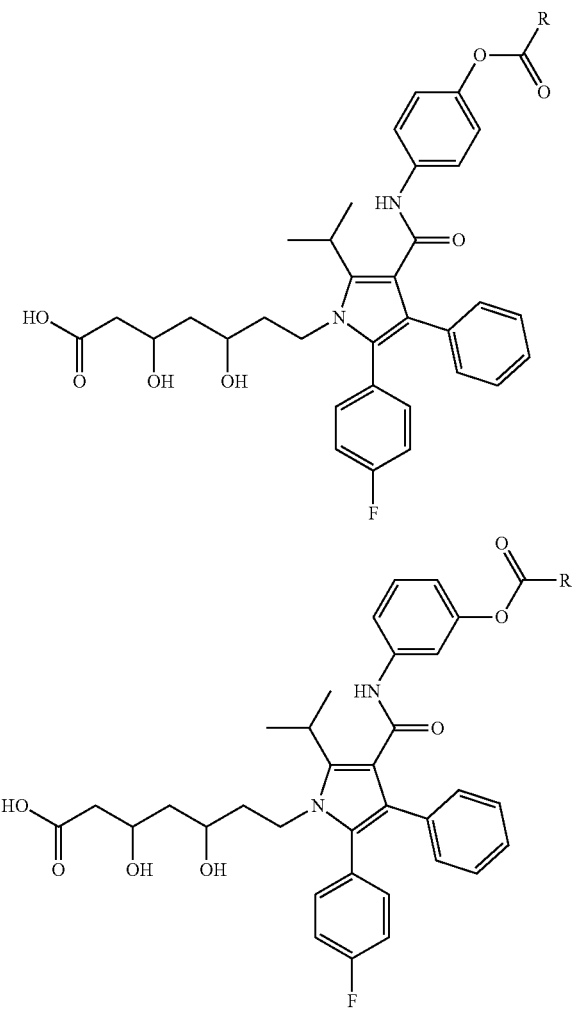

Rosuvastatin and related statins also can be linked to one or two agents, which can be the same or different, indicated by R in the formula below, which depicts the open form of rosuvastatin.

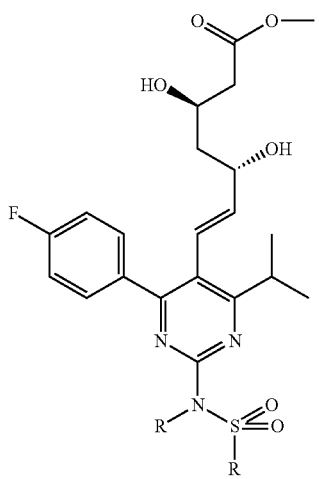

Lovastatin and related statins can be linked to a therapeutic agent, R, via, for example, an ester or amide linkage as depicted below:

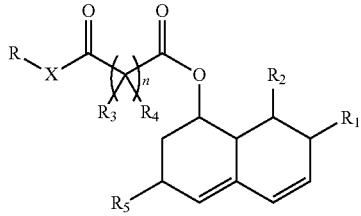

wherein R is a therapeutic agent;
n is 1, 2, 3, 4, 5, or 6;
X is S, O or N;
$R_3$ and $R_4$ are independently selected from —$CH_3$, —OH, H, a halogen,
—$CH_2CH_3$ and cyclopropyl
$R_1$ and $R_5$ are independently selected from —$CH_3$ and H; and
$R_2$ is selected from:

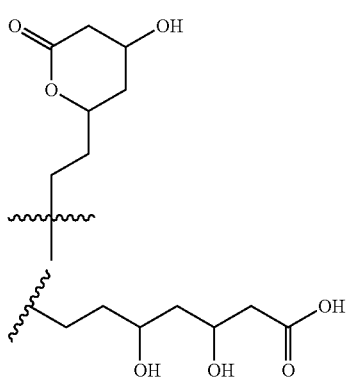

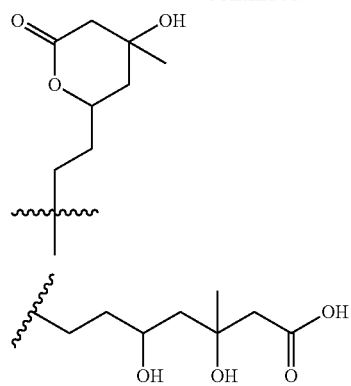

Simvastatin, depicted below, can be linked to various therapeutic agents.

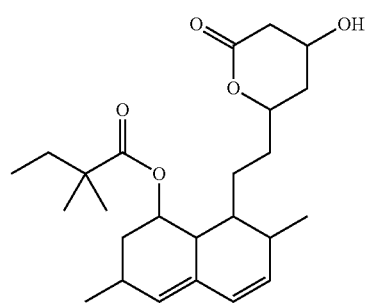 [SMILES: CCC(C)(C)C(=O)OC1CC(C)C=C2C=CC(C)C(CCC3CC(O)CC(=O)O3)C21]

For example, a therapeutic agent, R, could be conjugated to simvastatin or a related statin in any configuration depicted below.

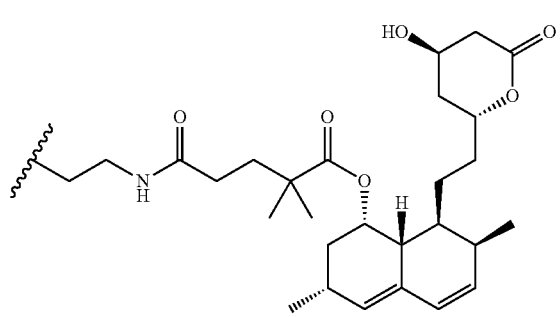

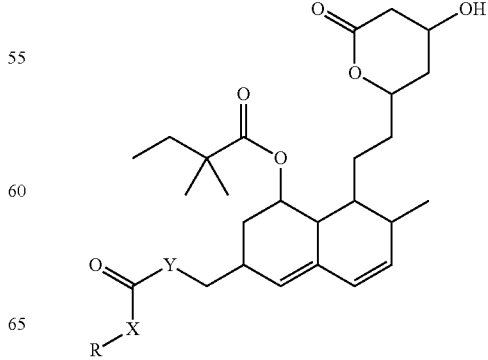

-continued

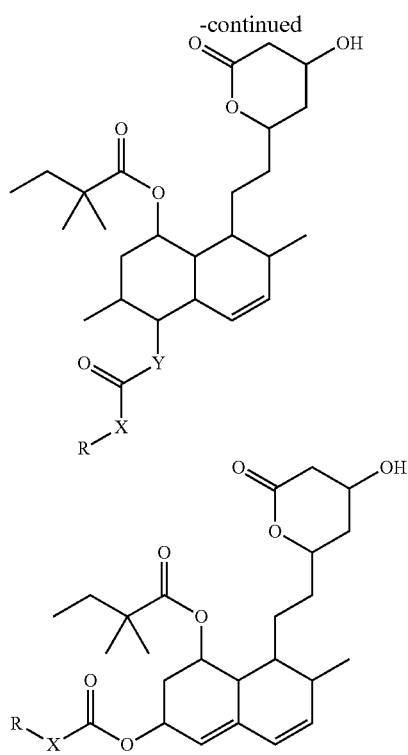

X = alkyl, O, N, S
Y = alkyl, O, N, S

Of course, a therapeutic agent could be conjugated to lovastatin as depicted above for simvastatin.

Useful therapeutic conjugates include niacin linked to simvastatin through a linker as depicted below

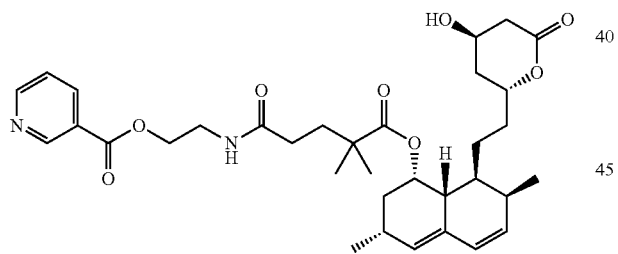

Another useful therapeutic conjugate comprises ibuprofen linked to simvastatin as depicted below.

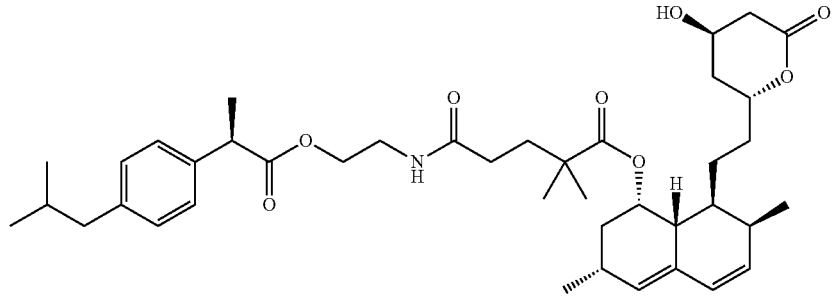 [SMILES: CC(C)Cc1ccc([C@@H](C)C(=O)OCCNC(=O)CCC(C)(C)C(=O)O[C@H]2C[C@@H](C)C=C3C=C[C@H](C)[C@H](CC[C@@H]4C[C@@H](O)CC(=O)O4)[C@H]32)cc1]

Useful conjugates include those having Formula III

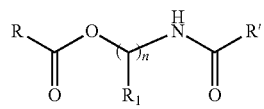

Formula III wherein R' is a statin; R is a therapeutic agent; n is 1, 2, 3, 4, or 5; each $R_1$ is independently: H, —COOH, lower alkyl (e.g., a C1 to C6 alkyl), a primary amine, a secondary amine, a tertiary amine, a halogen. When the therapeutic agent is attached to the linker via a carboxyl group, conjugates having Formula III can undergo processing in the body to release the therapeutic agent with an intact carboxyl group.

A number of different conjugates are available where the therapeutic agent has the structure:

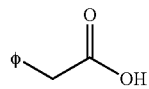

wherein Φ represents the portion of the therapeutic molecule not depicted in detail. A statin or statin derivative having the structure:

wherein Ω represents the portion of the statin molecule not depicted in detail and X is O, S, or N, can be linked to such therapeutic agents via linker to create a conjugate having any of the following structures (in which n is 0, 1, 2, 3, 4, 5 or 6):

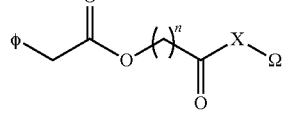

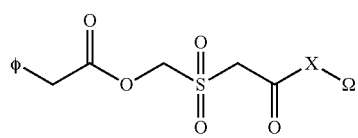

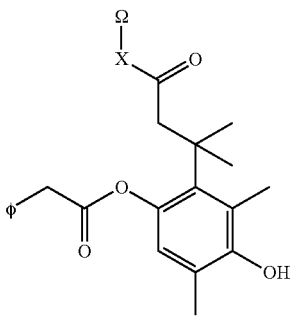

Where the therapeutic agent has the structure:

wherein Φ represents the portion of the therapeutic molecule not depicted in detail and the statin or statin derivative has the structure:

HX-Ω wherein Ω represents the portion of the statin or statin derivative molecule not depicted in detail and X is O, S, or N, the following conjugates can be useful:

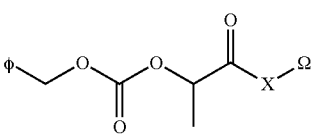

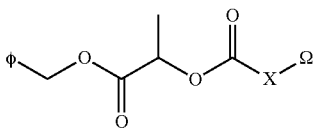

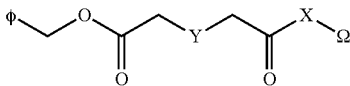

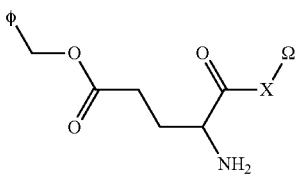

wherein Y is O, S, S(O), S(O)$_2$.

Statins Linked to Nucleic Acid Molecules

Statins can be linked to nucleic acid molecules to deliver the nucleic acid molecules to liver cells. For example, a statin can be linked to an antisense molecule directed against a hepatitis virus (e.g., hepatitis virus A, B, C, D or E). A number of antisense molecules have been suggested as suitable for treatment or prevention of hepatitis C. For example, U.S. Pat. No. 6,608,191 describes an antisense molecule having the sequence gtgctcatgg tgcacggtct (SEQ ID NO:1), among others and explains that antisense molecules are desirably targeted to the 5' end hairpin loop, 5' end 6-base-pair repeats, 5' end untranslated region, polyprotein translation initiation codon, core protein coding region, ORF 3 translation initiation codon, 3'-untranslated region, 3' end palindrome region, R2 sequence and 3' end hairpin loop region of hepatitis C RNA. Other oligonucleotides can selectively interact with a nucleic acid molecule that includes a selected sequence without being strictly complementary or at all complementary to the selected sequence.

The oligonucleotides can include nucleotide or nucleoside monomers consisting of naturally-occurring bases and sugar connected by naturally-occurring internucleotide linkages. The oligonucleotides can also include non-naturally-occurring monomers that confer a desirable property, e.g., nuclease resistance or increased affinity in hybridization to a nucleic acid molecule. Thus, the oligonucleotides can include phosphorothioates, phosphotriesters, methyl phosphonates, short chain alkyl or cycloalkyl backbone linkages or short chain heteroatomic or heterocyclic backbone linkages at one or more positions instead of the naturally-occurring phosphodiester backbone. Methylene(methylimino) and morpholino backbones are useful (U.S. Pat. No. 5,034,506) as are protein-nucleic acid or peptide-nucleic acid (PNA) backbones in which the phosphodiester backbone of the oligonucleotide is replaced with a polyamide backbone, the bases being bound directly or indirectly to the aza nitrogen atoms of the polyamide backbone (Nielsen et al. 1991 Science 254:1497). Oligonucleotides can also include substitutions (methoxyethoxy, propoxy, OH, SH, SCH$_3$, F, OCN, OCH$_3$, C$_1$-C$_{10}$ alkyl, alkoxyalkoxy, substituted lower alkyl, alkaryl or aralkyl; Cl; Br; CN; CF$_3$; NH$_2$) at one or more positions, e.g., the 2' position. The oligonucleotide can include a group for improving the pharmacokinetic properties of the oligonucleotide or a group for improving the pharmacodynamic properties of the oligonucleotide. Similar modifications may also be made at other positions on the oligonucleotide (e.g., the 3' position of the sugar on the 3' terminal nucleotide and the 5' position of the sugar on the 5' terminal nucleotide. Oligonucleotides may also have sugar mimetics such as cyclobutyls in place of the pentofuranosyl group.

The nucleotides can include bases such as hypoxanthine, 6-methyladenine, 5-methylcytosine, 5-hydroxymethylcytosine, 5-bromouracil, 5-hydroxymethyluracil, 8-azaguanine, 7-deazaguanine, and 2,6-diaminopurine.

The statin can be linked to the oligonucleotide via a phosphate in the nucleotide backbone as shown schematically below.

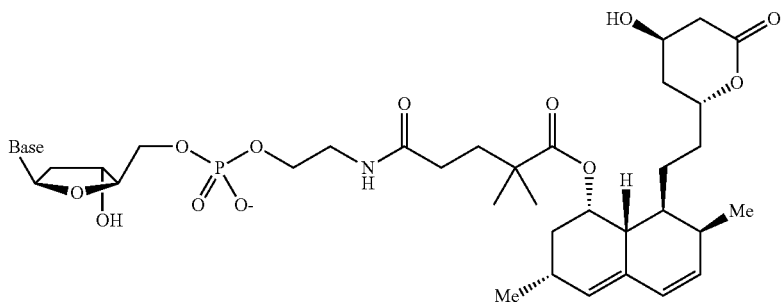

However, the statin can also be linked at the 3' position of the sugar of the 3' terminal nucleotide, the 5' position of the sugar of the 5' terminal nucleotide, or at the 2' position of the sugar of any nucleotide.

Example 1

Indomethacin-Simvastatin

A compound (6(R)-[2-[8(S)-{4-(2-{2-[1-(4-Chloro-benzoyl)-5-methoxy-2-methyl-1H-indol-3-yl]-acetoxy}-ethyl-carbamoyl)-2,2-dimethyl-butyryloxy}-2(S),6(R)-dimethyl-1,2,6,7,8,8,a(R)-hexahydronaphthyl-1(S)]ethyl]-4(R)-hydroxy-3,4,5,6-tetrahydro-2H-Pyran-2-one (10a) having indomethacin covalently linked to simvastatin through a linker was prepared as follows.

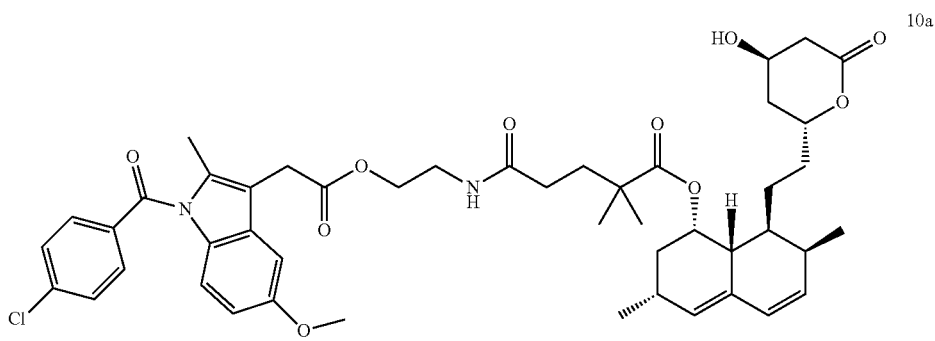 [SMILES: COc1ccc2c(c1)c(CC(=O)OCCNC(=O)CCC(C)(C)C(=O)O[C@H]1C[C@@H](C)C=C3C=C[C@H](C)[C@H](CC[C@@H]4C[C@@H](O)CC(=O)O4)[C@H]31)c(C)n2C(=O)c1ccc(Cl)cc1]

Step 1

Preparation of 2,2-Dimethyl-pentanedioic acid 5-allyl ester (2)

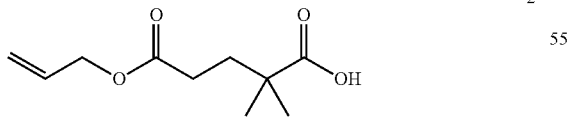

A mixture of dihydro-3,3-dimethyl-3H-pyran-2,6-dinone (111 mg, 0.78 mmol), allyl alcohol (60 µl, 0.78 mmol) and 4-dimethylaminopyridine (1 mg, 0.008 mmol) in 2,6-di-tert-butylpyridine (5 mL) was stirred at ambient temperature for 16 h. The reaction mixture was diluted with $CH_2Cl_2$ (16 mL) and washed with 1N HCl. After drying with $MgSO_4$ and filtration, the organic layer was evaporated to give crude residue which was chromatographed on a silica gel column using a gradient solvent system consisting of hexane:ethyl acetate from 0 to 50% ethyl acetate to yield the title compound, 2 (125.9 mg, 81%) as a colorless oil.

$^1$H-NMR (CDCl$_3$) δ 5.90 (1H, ddt, J=17.2, 10.4, 5.6 Hz), 5.30 (1H, dm, J=17.2, 1.6 Hz), 5.23 (1H, dm, J=10.8 Hz), 4.56 (2H, dt, J=6.0, 1.6 Hz), 2.39-2.35 (2H, m), 1.93-1.88 (2H, m), 1.21 (6H, s); $^{13}$C-NMR (CDCl$_3$) δ 183.94, 172.98, 132.07, 118.34, 65.21, 60.41, 41.49, 34.74, 30.06, 24.76, 14.14.

Step 2

Preparation of 2,2-Dimethyl-pentanedioic acid 5-allyl ester 1-(8-{2-[4-(tert-butyl-dimethyl-silanyloxy)-6-oxo-tetrahydro-pyran-2-yl]-ethyl}-3,7-dimethyl-1,2,3,7,8,8a-hexahydro-naphthalen-1-yl)ester (5)

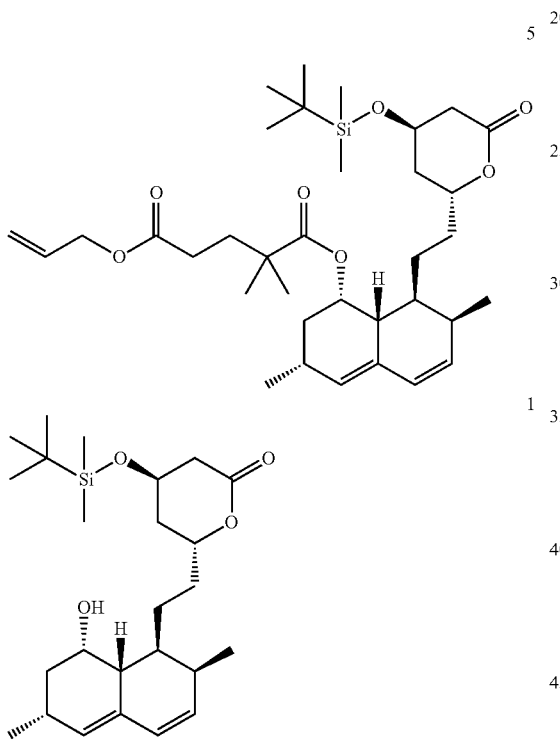

To a solution of 2 (4.7 g, 23.5 mmol) in CH$_2$Cl$_2$ (16 mL) was added oxalyl chloride (6.7 mL, 76.8 mmol) dropwise under nitrogen at ambient temperature. The resulting solution was stirred under nitrogen at ambient temperature overnight. Evaporation of the reaction mixture to dryness gave acid chloride, which was added dropwise to a solution of 1 (2.16 g, 4.97 mmol) and dry lithium chloride (4.7 g, 111.9 mmol) in dry pyridine (24 mL) under nitrogen at ambient temperature. The resulting mixture was heated to 85° C. under nitrogen overnight. After being cooled to ambient temperature, the reaction mixture was evaporated to remove pyridine and diluted with ethyl acetate then washed with 10% citric acid. After drying with MgSO$_4$ and filtration, the organic layer was evaporated to give crude residue which was chromatographed on a silica gel column using a gradient solvent system consisting of hexane:ethyl acetate from 0 to 70% ethyl acetate to yield the title compound, 5 (3.47 g, 76%) as a colorless oil.

$^1$H-NMR (CDCl$_3$) δ 5.97 (1H, d, J=9.5 Hz), 5.88 (1H, ddt, J=10.5, 6.5, 6.0 Hz), 5.77 (1H, dd, J=9.5, 6.0 Hz), 5.50 (1H, t, J=3.25 Hz), 5.36-5.34 (1H, m), 5.29 (1H, dm, J=17.5 Hz), 5.22 (1H, dm, J=10.0 Hz), 4.62-4.57 (1H, m), 4.56-4.54 (2H, m), 4.29 (1H, quint, J=3.5 Hz), 2.60 (1H, dd, J=12.0, 4.5 Hz), 2.57-2.53 (1H, m), 2.46-2.40 (1H, m), 2.40-2.34 (1H, m), 2.33-2.29 (2H, m), 2.28-2.23 (1H, m), 1.86-1.95 (2H, m), 1.92-1.80 (4H, m), 1.69-1.56 (2H, m), 1.48-1.23 (3H, m), 1.16 (3H, s), 1.15 (3H, s), 1.06 (3H, d, J=7.5 Hz), 0.89 (3H, d, J=7.5 Hz), 0.88 (9H, s), 0.76 (3H, s), 0.07 (3H, s); $^{13}$C-NMR (CDCl$_3$) δ 176.87, 172.88, 170.28, 132.94, 132.13, 131.48, 129.61, 128.31, 118.29, 76.46, 68.41, 65.14, 63.53, 42.00, 39.29, 37.43, 36.76, 36.76, 36.60, 34.66, 33.02, 32.79, 30.62, 30.04, 27.21, 25.66, 25.21, 24.80, 24.18, 23.09, 17.93, 13.84, −4.89; ESI-MS; 617.4 [M$^+$+H], 639.3 [M$^+$+Na]

Step 3

Synthesis of 6(R-[2-[8(S)-(4-Hydroxycarbonyl-2,2-dimethyl-butyryloxy-2(S),6(R)-dimethyl-1,2,6,7,8,8,a(R)-hexahydronaphthyl-1(S)]ethyl]-4(R)-tert-butyl-dimethyl-silanyloxy-3,4,5,6-tetrahydro-2H-Pyran-2-one (6)

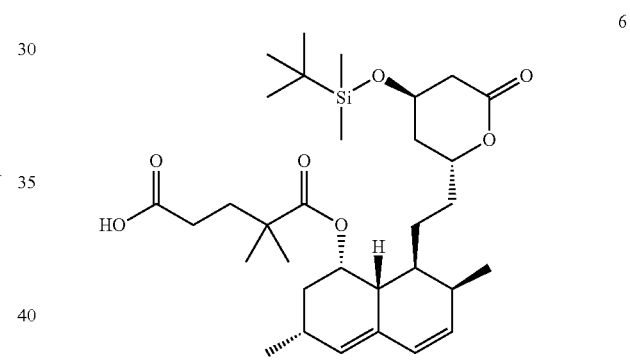

To a solution of 5 (3.11 g, 5.05 mmol) and triphenylphosphine (264.9 mg, 1.01 mmol) in CH$_2$Cl$_2$ (50 mL) was added 2M diethylammonium formate in CH$_2$Cl$_2$ (5 mL, 10.1 mmol). The resulting solution was stirred under nitrogen at ambient temperature for 1 min. Tetrakis-triphenylphosphine palladium (291.7 mg, 0.252 mmol) was added to the solution. The resulting mixture was stirred under nitrogen at ambient temperature for 3 h. The reaction was diluted with ethyl acetate and 1M KHSO$_4$ was added to the mixture to acidify (ca. pH 2). The organic layer was washed with brine. After drying with MgSO$_4$ and filtration, the organic layer was evaporated to give crude residue which was chromatographed on a silica gel column using a gradient solvent system consisting of CHCl$_3$:MeOH from 1 to 10% MeOH to yield the title compound, 6 (2.86 g, 98%) as a slightly yellowish white amorphous powder.

$^1$H-NMR (CDCl$_3$) δ 5.98 (1H, d, J=9.6 Hz), 5.77 (1H, dd, J=9.6, 6.0 Hz), 5.50 (1H, s), 5.32-5.30 (1H, m), 4.62 (1H, dt, J=7.2, 2.6 Hz), 4.29 (1H, quint, J=3.6 Hz), 2.61 (1H, dd, J=17.2, 4.4 Hz), 2.60-2.52 (1H, m), 2.47-2.39 (1H, m), 2.39-2.30 (2H, m), 2.30-2.20 (1H, m), 2.04-1.75 (5H, m), 1.72-1.60 (2H, m), 1.51-1.29 (3H, m), 1.27-1.19 (2H, m), 1.17 (3H, s), 1.16 (3H, s), 1.06 (3H, d, J=7.2 Hz), 0.89 (3H, d, J=7.2 Hz), 0.88 (9H, s), 0.09 (3H, s), 0.08 (3H, s)

Step 4

Synthesis of 6(R)-[2-[8(S)-(4-Hydroxycarbonyl-2,2-dimethyl-butyryloxy)-2(S),6(R)-dimethyl-1,2,6,7,8,8,a(R)-hexahydronaphthyl-1(S)]ethyl]-4(R)-hydroxy-3,4,5,6-tetrahydro-2H-Pyran-2-one (7)

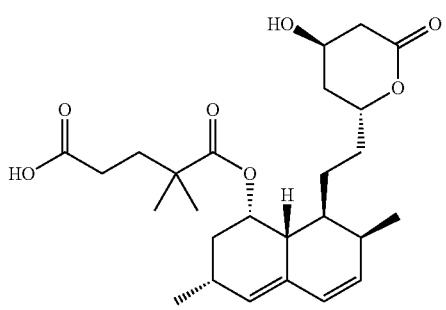

A mixture of 6 (2.46 mg, 4.27 mmol) and acetic acid (0.98 mL, 17.1 mmol) was stirred in 20 mL of dry THF under nitrogen at 0° C. for 1 min. To this solution was added dropwise tetra-butyl ammonium fluoride 1.0 M solution in THF (12.8 mL, 12.97 mmol) at 0° C. The resulting mixture was stirred under nitrogen at ambient temperature overnight. The reaction was diluted with ethyl acetate (210 mL) and washed with 1N HCl (5×350 mL) and brine. After drying with MgSO$_4$ and filtration, the organic layer was evaporated to give crude residue which was chromatographed on a silica gel column using a gradient solvent system consisting of CHCl$_3$:MeOH from 1 to 10% MeOH to yield the title compound, 7 (1.26 g, 64%) as a white amorphous powder.

$^1$H-NMR (CDCl$_3$) δ 5.85 (1H, d, J=10.0 Hz), 5.75 (1H, dd, J=9.75, 6.25 Hz), 5.48 (1H, s), 5.28 (1H, d, J=3.0 Hz), 4.60 (1H, dt, J=3.5, 7.5 Hz), 4.32 (1H, quint, J=4.0 Hz), 2.68 (1H, dd, J=17.5, 5.0 Hz), 2.61 (1H, dd, J=17.5, 2.5 Hz), 2.38-2.46 (1H, m), 2.37-22.1 (4H, m), 2.02-1.83 (4H, m), 1.82-1.63 (4H, m), 1.48-1.29 (3H, m), 1.15 (3H, s), 1.13 (3H, s), 1.03 (3H, d, J=7.5 Hz), 0.86 (3H, d, J=6.5 Hz); ESI-MS; 463.2 [M$^+$+H], 485.1 [M$^+$+Na]

Step 5

6(R)-[2-[8(S)-{4-[(2,5-Dioxo-pyrrolidin-1-yl)oxycarbonyl]-2,2-dimethyl-butyryloxy}-2(S),6(R)-dimethyl-1,2,6,7,8,8,a(R)-hexahydronaphthyl-1(S)]ethyl]-4(R)-hydroxy-3,4,5,6-tetrahydro-2H-Pyran-2-one (8)

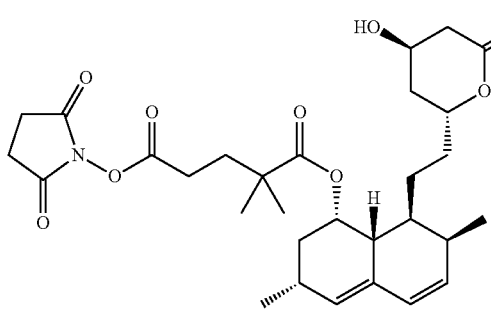

A mixture of 7 (55.4 mg, 0.120 mmol) and N-hydroxysuccinimide (14.0 mg, 0.120 mmol), was stirred in 2 mL of dry CH$_2$Cl$_2$ under nitrogen for 1 min. N-Cyclohexylcarbodiimide, N'-methyl polystyrene (>1.30 mmol/g) (184.0 mg, 0.240 mmol) was added and the mixture was stirred under nitrogen at ambient temperature overnight. The spent resin was removed by filtration and washed with CH$_2$Cl$_2$. Evaporation of the filtrate provided the title compound, 8 (64.8 mg, 97%) as a white amorphous powder.

$^1$H-NMR (CDCl$_3$) δ 5.97 (1H, d, J=9.5 Hz), 5.77 (1H, dd, J=9.75, 6.25 Hz), 5.52-5.50 (1H, m), 5.38-5.36 (1H, m), 4.62-4.56 (1H, m), 4.33-4.30 (1H, m), 2.84 (4H, s), 2.71 (1H, dd, J=17.75, 5.25 Hz), 2.66-2.54 (2H, m), 2.50-2.40 (1H, m), 2.39-2.33 (1H, m), 2.29-2.24 (1H, m), 2.08-1.99 (1H, m), 1.98-1.93 (1H, m), 1.93-1.81 (3H, m), 1.74-1.59 (3H, m), 1.50-1.41 (2H, m), 1.37-1.23 (3H, m), 1.21 (3H, s), 1.18 (3H, s), 1.07 (3H, d, J=7.0 Hz), 0.88 (3H, d, J=7.0 Hz); ESI-MS; 582.3 [M$^+$+Na]

Step 6

Synthesis of 6(R)-[2-[8(S)-{4-(2-Hydroxy-ethylcarbamoyl)-2,2-dimethyl-butyryloxy}-2(S),6(R)-dimethyl-1,2,6,7,8,8,a(R)-hexahydronaphthyl-1(S)]ethyl]-4(R)-hydroxy-3,4,5,6-tetrahydro-2H-Pyran-2-one (9)

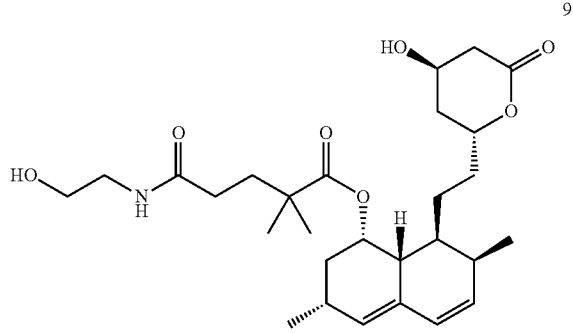 [SMILES: C[C@H]1C=C2C=C[C@H](C)[C@H](CC[C@@H]3C[C@@H](O)CC(=O)O3)[C@H]2[C@@H](OC(=O)C(C)(C)CCC(=O)NCCO)C1]

A mixture of 8 (10 mg, 0.018 mmol) and ethanolamine (1.3 μL, 0.021 mmol) in dry CH$_2$Cl$_2$ was stirred under nitrogen at ambient temperature overnight. The reaction mixture was diluted with brine and extracted with ethyl acetate. After drying with MgSO4 and filtration, the organic layer was evaporated to give crude residue which was chromatographed on a silica gel column using a gradient solvent system consisting of CHCl$_3$:MeOH from 1 to 10% MeOH to yield the title compound, 9 (8.7 mg, 96%) as a white amorphous powder.

$^1$H-NMR (CDCl$_3$) δ 6.57 (1H, s), 5.98 (1H, d, J=10 Hz), 5.77 (1H, dd, J=9.8, 6.2 Hz), 5.52 (1H, s), 5.30 (1H, d, J=3.2 Hz), 4.73-4.68 (1H, m), 4.35-4.32 (1H, m), 3.74-3.62 (2H, m), 3.48-3.39 (2H, m), 3.36-3.28 (2H, m), 2.68 (1H, dd, J=17.6, 4.8 Hz), 2.65-2.60 (1H, m), 2.50-2.40 (1H, m), 2.39-2.31 (1H, m), 2.30-2.14 (1H, m), 2.04-1.90 (3H, m), 1.81-1.62 (4H, m), 1.49-1.34 (2H, m), 1.32-1.21 (2H, m), 1.18 (3H, s), 1.15 (3H, s), 1.06 (3H, d, J=7.2 Hz), 0.88 (3H, d, J=6.8 Hz); ESI-MS; 506.1 [M$^+$+H], 528.3 [M$^+$+Na]

Step 7

Synthesis of 6(R)-[2-[8(S)-{4-(2-{2-[1-(4-Chloro-benzoyl)-5-methoxy-2-methyl-1H-indol-3-yl]-ac-etoxy}-ethylcarbamoyl)-2,2-dimethyl-butyryloxy}-2(S),6(R)-dimethyl-1,2,6,7,8,8,a(R)-hexahydronaphthyl-1(S)]ethyl]-4(R)-hydroxy-3,4,5,6-tetrahydro-2H-Pyran-2-one (10a)

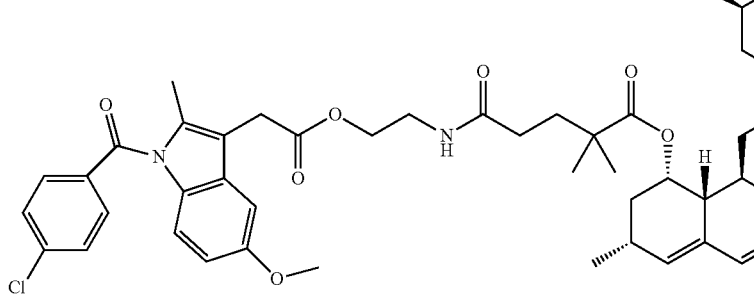

A mixture of 9 (88.3 mg, 0.175 mmol), Indomethacin (80.4 mg, 0.225 mmol), and 4-dimethylaminopyridine (21.3 mg, 0.175 mmol) were stirred in 3 mL of dry THF under nitrogen for 5 min. N-Cyclohexylcarbodiimide, N'-methyl polystyrene (>1.30 mmol/g) (268 mg, 0.349 mmol) was added and the mixture was stirred under nitrogen at ambient temperature overnight. The spent resin was removed by filtration and washed with THF. The filtrate was evaporated. The residue was purified by column chromatography on silica gel using a gradient solvent system consisting of $CHCl_3$:MeOH from 1 to 10% MeOH to yield the title compound, 10a (12.7 mg, 9%) as a white amorphous powder.

$^1$H-NMR ($CDCl_3$) δ 7.67 (2H, d, J=8.25 Hz), 7.48 (2H, d, J=8.25 Hz), 6.95 (1H, d, J=2.8 Hz), 6.88 (1H, d, J=9.0 Hz), 6.67 (1H, dd, J=9.2, 2.4 Hz), 6.27 (1H, t, J=7.75 Hz), 5.97 (1H, d, J=9.5 Hz), 5.76 (1H, dd, J=9.5, 6.0 Hz), 5.51 (1H, s), 5.27 (1H, s), 4.68-4.58 (1H, m), 4.29 (1H, s), 4.22 (1H, dd, J=Hz), 4.15 (1H, dd, J=Hz), 3.84 (3H, s), 3.70 (2H, s), 3.56-3.34 (2H, m), 2.66 (1H, dd, J=18.0, 4.75 Hz), 2.64-2.58 (1H, m), 2.48-2.41 (1H, m), 2.36 (3H, s), 2.36-2.29 (1H, m), 2.28-2.21 (1H, m), 2.12-1.97 (3H, m), 1.95-1.81 (3H, m), 1.79-1.64 (3H, m), 1.45-1.36 (2H, m), 1.34-1.22 (2H, m), 1.14 (3H, s), 1.11 (3H, s), 1.06 (3H, d, J=7.0 Hz), 0.87 (3H, d, J=7.0 Hz); ESI-MS; 845.3 [M$^+$+H]

Example 2

Indomethacin-Simvastatin Conjugate Protects Against Hepatic Injury

An indomethacin-simvastatin conjugate (Ind-S) and lovastatin alone were evaluated for possible hepatoprotective activity in a mouse model of hepatic injury induced by carbon tetrachloride ($CCl_4$). Ind-S at 0.5, 1 and 5 μmol/kg and lovastatin at 30 mg/kg were each administered intraperitoneally 0.5 hour before and at 4 and 8 hours after $CCl_4$ challenge. The degree of hepatic injury was manifested by increases in alanine aminotransferase (ALT) and aspartate aminotransferase (AST) levels relative to the vehicle-treated animals. A decrease of 30% or more in serum ALT or AST is considered significant protective activity.

Test Substances and Dosing Pattern

The test substances were provided at the indicated concentrations. The vehicle control was 2% Tween 80/0.9% NaCl. The test substances were administered intraperitoneally at 0.5 hour before and 4 and 8 hours after $CCl_4$ administration to test mice. The dosing volume was 5 mL/kg.

Animals

Male ICR derived mice weighing 24±2 g and provided by BioLasco Taiwan, a Charles River Laboratories Technology Licensee, were used in the study Space allocation for animals was 29×18×13 cm for 10 mice. The animals were housed in APEC$^R$ cages. All animals were maintained in a hygienic environment under controlled temperature (22-24° C.) and humidity (60%-70%) with 12 hours light/dark cycles for at least one week prior to use with free access to standard lab chow (LabDiet Rodent Diet, PMI Nutrition International, USA) and tap water.

Hepatic Injury Model

Seven groups of five ICR derived male mice (weighing 24±2 g) were used. Each animal was challenged with a single dose of carbon tetrachloride ($CCl_4$, 0.1 mL/kg in 50% olive oil, PO). The test substances were administered intraperitoneally at 30 minutes before and 4, 8 hours after carbon tetrachloride challenge and the animals were sacrificed 24 hours later. Serum alanine aminotransferase (ALT) and aspartate aminotransferase (AST) levels were measured by optimized UV method using a HITACHI automatic analyzer (model 7050). Silymarin (300 mg/kg, PO) as the positive control agent was administered orally to test animals at the same time.

Results and Analysis

Ind-S at 5 μmol/kg caused a significant reduction (34%) of AST activity relative to the vehicle-treated group; concomitantly a moderate but non-significant (21%) reduction in serum ALT level was observed, as shown in FIG. 1. However, Ind-S at 0.5 and 1 μmol/kg caused elevation in serum AST and ALT levels (7% to 23%) relative to the vehicle control group. Lovastatin (30 mg/kg, IP) and indomethacin (5 μmol/kg, IP) caused further increases in serum ALT (17% and 39%, respectively) and AST (38% and 73%, respectively) compared to the vehicle control. Silymarin (300 mg/kg, PO) caused significant reduction in serum ALT (50%) and AST (42%) relative to the vehicle-treated group. It is concluded that Ind-S at 5 μmol/kg (IP), but not at 0.5 and 1 μmol/kg demonstrated significant hepatoprotective activity against hepatic injury induced by carbon tetrachloride ($CCl_4$) in ICR mice, whereas lovastatin alone (30 mg/kg, IP) and indomethacin alone (5 μmol/kg×3) actually aggravated elevations in serum ALT and AST due to CCl₄.

Example 3

Inhibition of HMGCoA Reductase

A variety of conjugates were prepared and tested for the ability to inhibit rat HMGCoA reductase in vitro. The conjugates tested included: indomethacin-simvastatin conjugate (In—S); sulindac-simvastatin conjugate (Su-S); naproxen-simvastatin conjugate (Na—S); ibuprofen-simvastatin conjugate (Ib-S); niacin-simvastatin conjugate (Ni—S); and oligonucleotide-simvastatin conjugate (Ol-S). Lovastatin was used as a control. As shown in FIG. 2, all of the conjugates had an $IC_{50}$ in the nanomolar range indicating that conjugation does not eliminate the activity of simvastatin.

Example 4

Synthesis of Oligonucleotide-Targeting Agent Conjugates

An oligonucleotide can be conjugated at its 3' end to a statin or other targeting agent using the procedure shown in FIG. 3 or any other suitable procedure. Briefly, the 3' amino modifier solid support is first functionalized with the targeting agent. Next the oligonucleotide is synthesized on the support (FIG. 3; Route B) using, for example, an ABI 392 or an Expedite DNA synthesizer. In one example, 300 mg (13.3 μmol) of 3'-amino modifier C7 CPG (Glen Research, Sterling Va.) was stirred using a Labquake shaker with 4 mL of 20% piperidine/DMF at room temperature for 30 min, then filtered, washed with CH₃CN, and dried. Afterward, the resin was treated with 5-10 equivalents of the targeting agent as N-hydroxy-succinimide ester in CH₃CN and stirred for 6-12 h at room temperature. Both Fmoc deprotection and conjugation steps were carried out twice. The dried support-targeting agent obtained this way can be treated with phenoxyacetyl anhydryde and stored at -20 or used directly for oligonucleotide synthesis following standard protocols, including ultramild synthesis, and then deprotection. Purification of the conjugates can be done either by using Poly-Pak cartridges (Glen Research) or by RP-HPLC.

An oligonucleotide can be linked at its 5' end to a statin or other targeting agent using the protocol depicted in FIG. 3 or any other suitable procedure. Using an ABI 392 DNA synthesizer, oligonucleotides were synthesized with C5-amino modifier (Glen Research, Sterling Va.) on the 5' terminus. After deprotection of the monomethyltrityl (MMT) group with trichloroacetic acid, the CPG was washed with copious amount of acetonitrile, dried and transferred to a dry eppendorf tube. Next, 20 equivalents of statin succinimide ester was dissolved in 10% triethylamine in acetonitrile and added to the CPG. The reaction was mixed using a Labquake shaker over 8 hours. The mixture was filtered, washed with acetonitrile and deprotected with 40% 2M NaOH in methanol for 6 hours at room temperature. After addition of 2M triethylammonium acetate (10% volume), the reaction mixture was dried using a speed-vac and purified using HPLC.

Example 5

Preparation of a 6α-Hydroxymethyl Metabolite of Lovastatin

Figure 5:
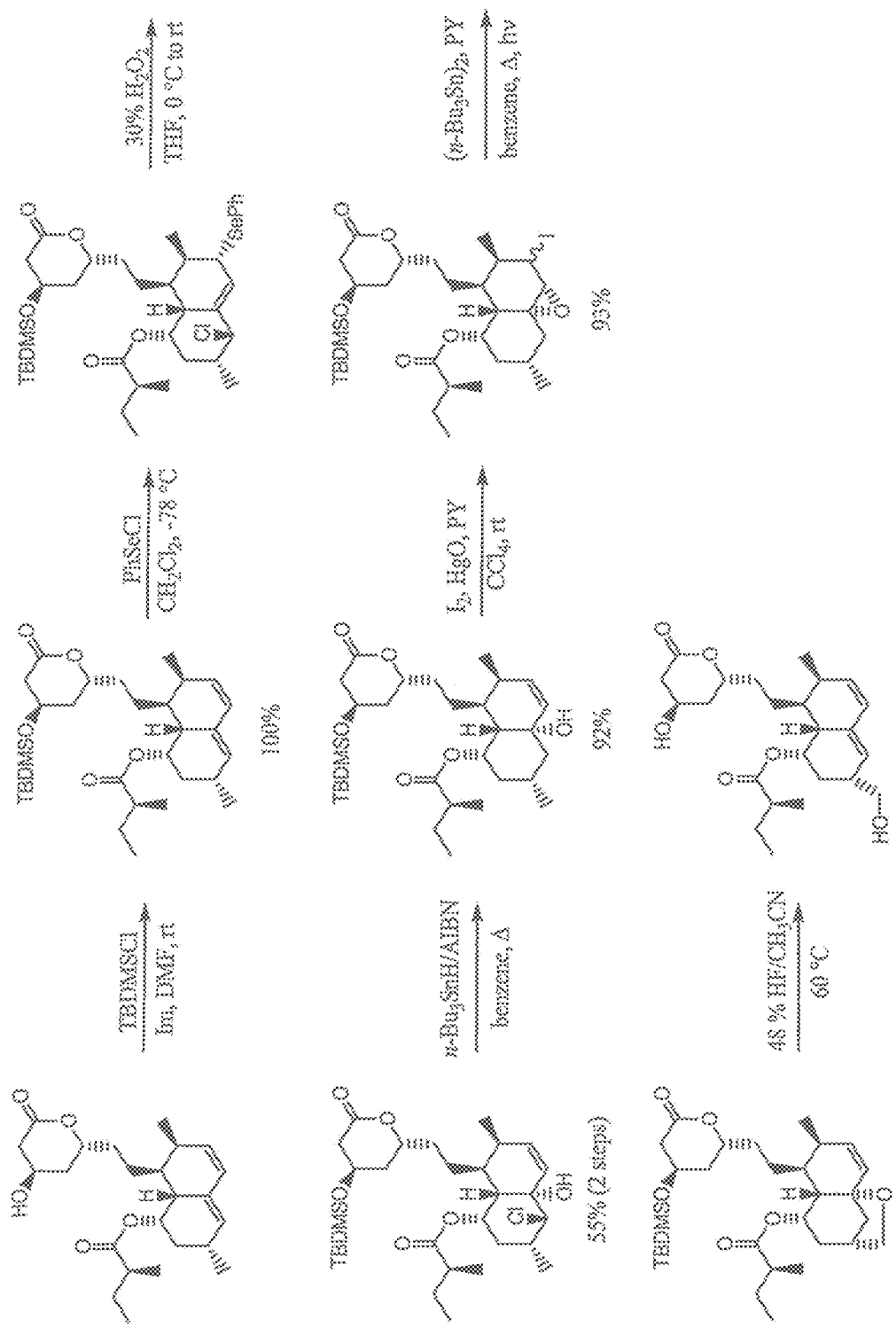
FIG. 5 is a schematic depiction of the preparation of 6α-hydroxymethyl metabolite of lovastatin modified so that it can be readily conjugated to a selected therapeutic agent.
Figure 5:
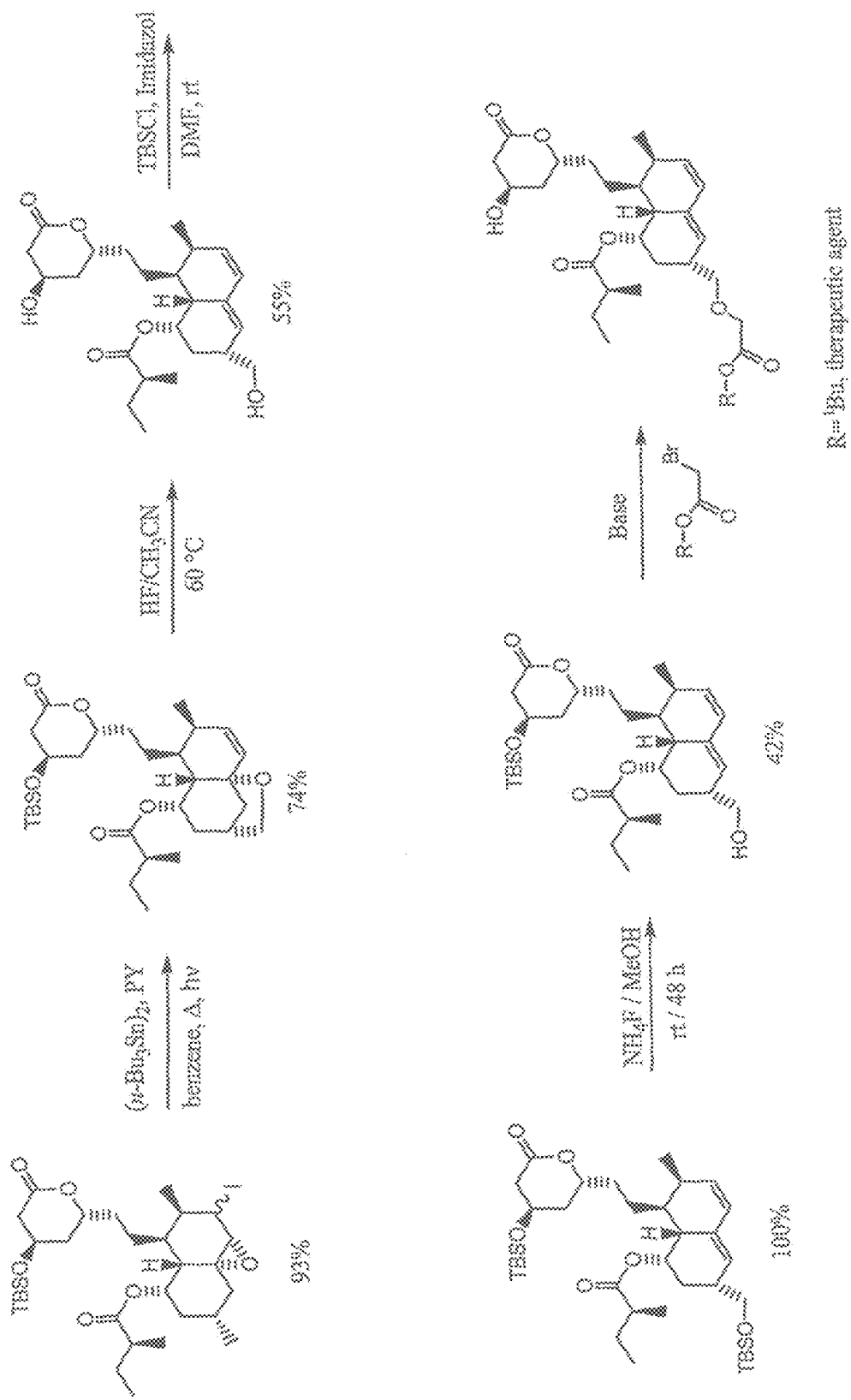

A 6α-hydroxymethyl metabolite of lovastatin can be used as a targeting agent. The metabolite can be prepared using a modification of a protocol for preparing simvastatin (J. Org Chem 57:1966, 1992) as shown in FIG. 5.

This lovastatin derivative can be modified by the addition of a therapeutic agent (R) to create conjugates that are targeted using the lovastatin derivative. In these conjugates, shown below, X is an alkyl group (e.g., C1-C8 alkyl), O, N or S; Z is an alkyl group (e.g., C1-C8 alkyl, N or O) and Y is O or S.

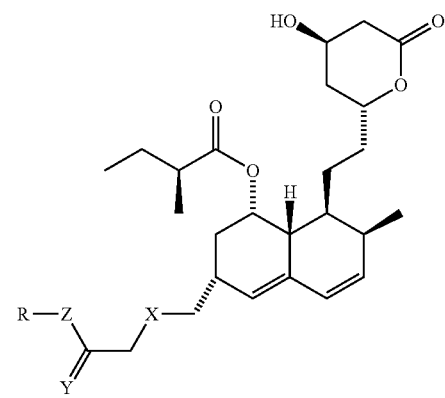

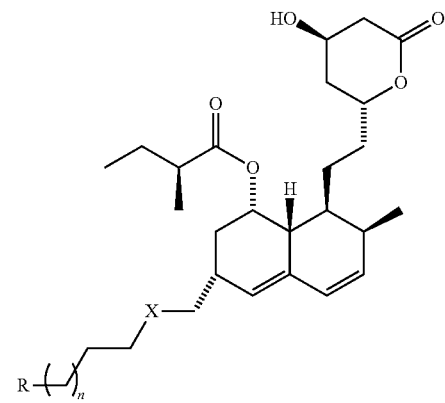

Example 6

Atorvastatin Derivatives

Figure 6:
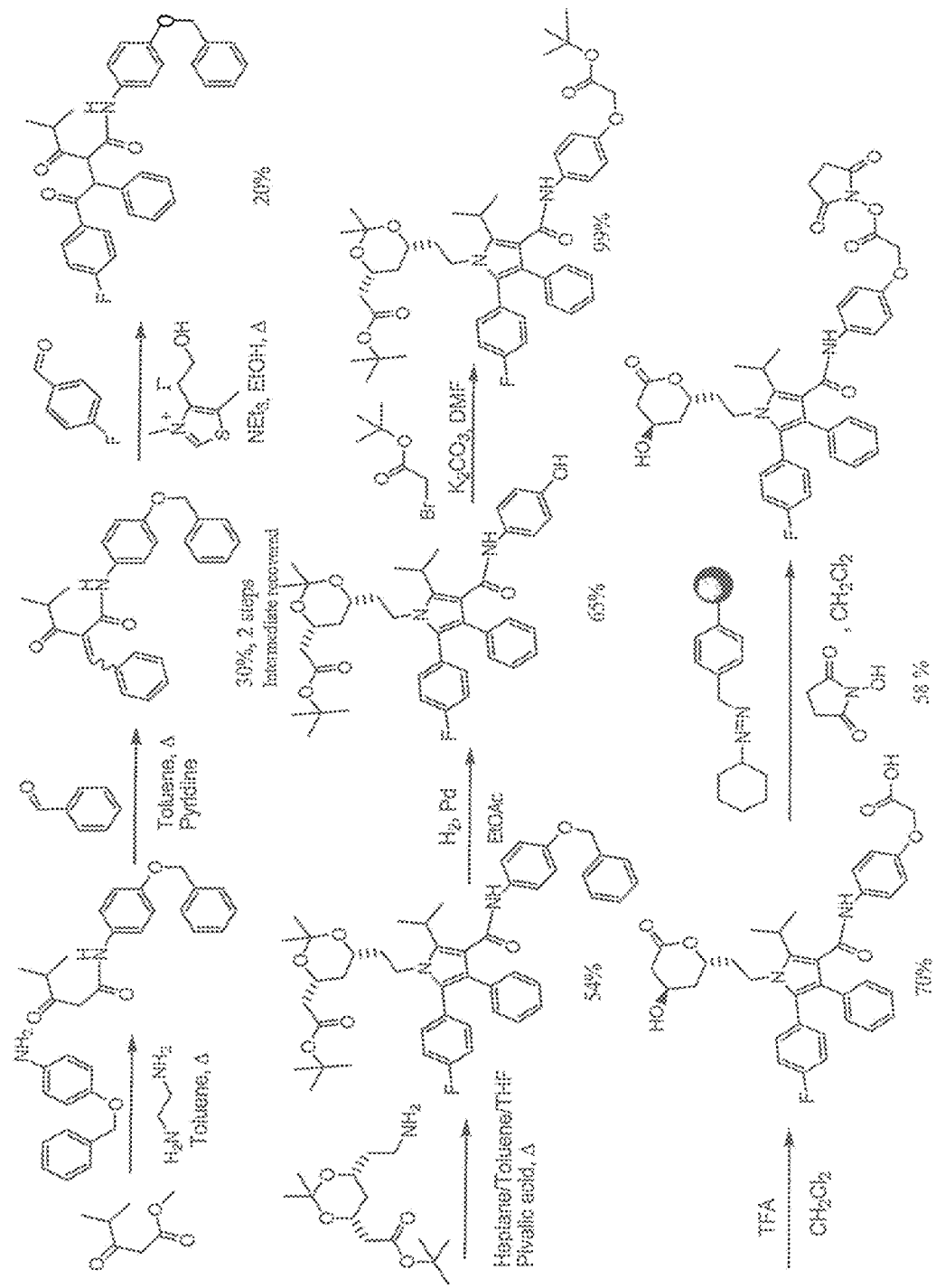
FIG. 6 is a schematic depiction of the preparation of an atorvastatin derivative that is suitable for conjugation to a selected therapeutic agent.

Atorvastatin can be prepared in a form suitable for derivatization using a modification of the method described in U.S. Pat. No. 5,385,929, as shown in FIG. 6. While this drawing shows one possible derivative of atorvastatin, many others are possible. The therapeutic agent (R) can be attached at any position on the ring at shown below, where n is 1, 2, 3, 4 or 5 and each R can be the same or different.

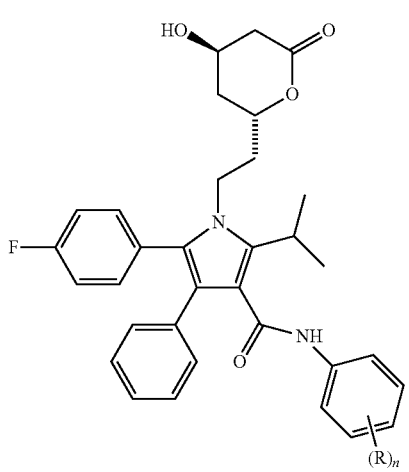

Figure 7:
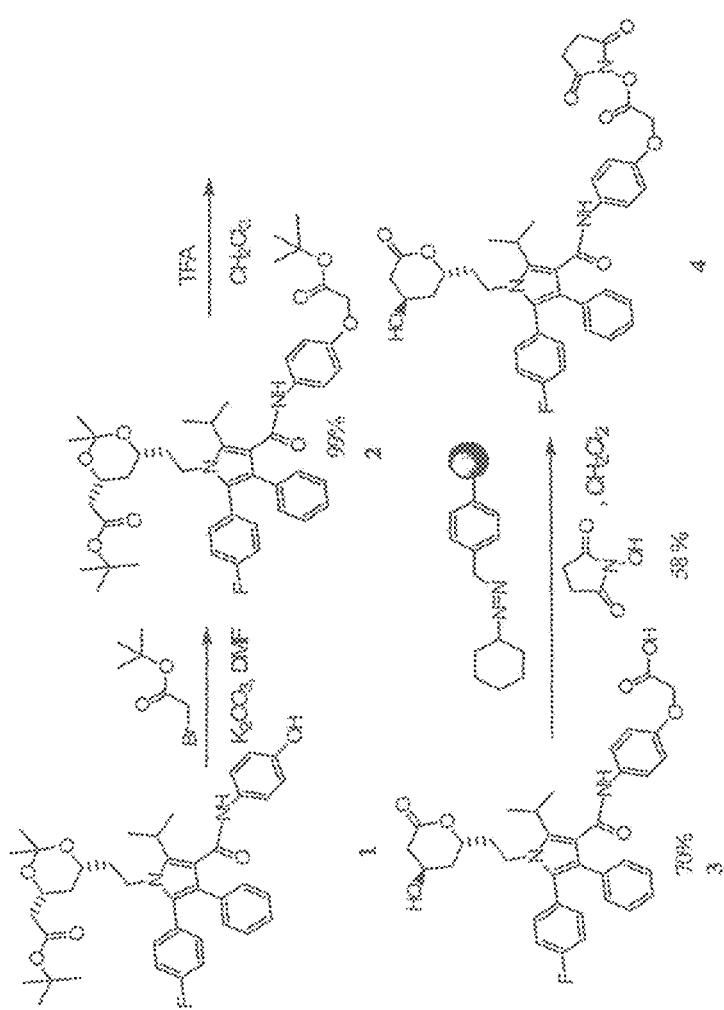
FIG. 7 is a schematic depiction of aspects of a scheme for preparing derivatives of atorvastatin.

For example, referring to the scheme and compound numbering in FIG. 7, A mixture of compound 1 (100 mg, 0.13 mmol), tert-butyl bromoacetate (46 mg, 0.23 mmol) and $K_2CO_3$ (56 mg, 0.46 mmol) in anhydrous DMF (2 mL) was stirred for 16 hours at room temperature. $CH_2Cl_2$ (10 mL) was added to the crude, which was washed with brine and then with water and dried over $MgSO_4$. Evaporation of the solvent provided the title compound 2 (102 mg, 99%) as a brownish oil, which was used in the next step without further purification. $^1$H-NMR (CDCl$_3$) δ 7.20-7.00 (m, 9H), 6.90-6.78 (m, 4H), 4.20 (m, 1H), 4.42 (bs, 2H), 4.05 (m, 1H), 3.80 (m, 1H), 3.70 (m, 1H), 3.56 (septet, 1H, J=7.3 Hz), 2.38 (1H, dd, J=17.6, 4.4 Hz), 2.22 (m, 1H), 1.90 (m, 1H), 1.75-1.70 (m, 3H), 1.60 (m, 1H), 1.54 (m, 6H), 1.45-1.50 (2s, 18H), 1.30-1.20 (2s, 6H). ESI-MS; 785.3 [M$^+$+H].

Compound 2 (100 mg, 0.13 mmol) was dissolved in 6 mL of $CH_2Cl_2$ and 0.3 mL of TFA was added dropwise. The reaction was stirred at room temperature overnight, after which the solvent was evaporated and the crude chromatographed on silica gel using a gradient solvent system consisting of $CH_2Cl_2$/MeOH from 50:2 to 4:1 to give the tittle compound 3 (56 mg, 70%), as a light brown solid. $^1$H-NMR (CDCl$_3$) δ 7.20-7.00 (m, 9H), 6.90-6.78 (m, 4H), 4.6 (bs, 2H), 4.52 (m, 1H), 4.34 (m, 1H), 4.26-4.19 (m, 1H), 4.06-4.00 (m, 1H), 3.56 (septet, 1H, J=7.3 Hz), 2.68 (1H, dd, J=17.6, 4.4 Hz), 2.59 (m, 1H), 1.90 (m, 1H), 1.75-1.70 (m, 3H), 1.60 (m, 1H), 1.54 (m, 6H). ESI-MS; 615.2 [M$^+$+H].

A mixture of 3 (46.5 mg, 0.075 mmol) and N-hydroxysuccinimide (9.6 mg, 0.18 mmol), was stirred in 5 mL of $CH_2Cl_2$ for 10 min. N-Cyclohexylcarbodiimide, N'-methyl polystyrene (>1.30 mmol/g, 116 mg, 0.15 mmol) was added and the mixture was stirred under nitrogen at ambient temperature overnight. The spent resin was removed by filtration and washed with $CH_2Cl_2$. The crude was separated by silica gel chromatography using a gradient solvent system consisting of Hexane\AcOEt, from 1:1 to AcOEt 100%, to provide the title compound, 4 (31 mg, 58%) as a light yellow foam. $^1$H-NMR (CDCl$_3$) δ 7.20-7.00 (m, 9H), 6.90-6.75 (m, 4H), 4.9 (bs, 2H), 4.52 (m, 1H), 4.34 (m, 1H), 4.26-4.19 (m, 1H), 4.06-4.00 (m, 1H), 3.56 (septet, 1H, J=7.3 Hz), 2.84 (4H, s), 2.68 (1H, dd, J=17.6, 4.4 Hz), 2.59 (m, 1H), 1.90 (m, 1H), 1.75-1.70 (m, 3H), 1.60 (m, 1H), 1.54 (m, 6H). ESI-MS; 712.1 [M$^+$+H]

Formulation and Administration of Agents

If the therapeutic conjugate is to be administered orally, it is can be formulated with an enteric coating. For example, the formulation can be provided with a non-porous, gastric acid-resistant polymer coating, e.g., a coating that is insoluble or sparingly soluble at pH 1.5 to pH 5, but is soluble above pH 5 or pH 5.5 up to or above pH 9. The polymer can include, for example, hydroxypropyl methyl cellulose phthalate, cellulose acetate phthalate, diethyl phthalate, dibutyl phthalate, and acrylic based polymers. The formulation can also be buffered by inclusion of a buffering agent, for example, sodium bicarbonate, potassium carbonate, potassium bicarbonate, ammonium carbonate, trimethylamine, tris-glycine, di-arginine, tri-arginine, poly-arginine, di-lysine, tri-lysine, poly-lysine, diethylamine and triethanolamine. The buffering agent can be designed to provide a pH of from about 7 to about 9 in the small intestine or large intestine of a human patient. The formulation can also include a disintegrant, e.g., ursodiol, starch, modified starches, microcrystalline cellulose and propylene glycol alginate.

Combination therapy can be achieved by administering a therapeutic conjugate with an additional therapeutic agent. The additional therapeutic agent administered in combination with the therapeutic conjugate can be for treatment of the same condition as the therapeutic conjugate or for treatment of a different condition. The therapeutic conjugate and the additional therapeutic agent can be formulated and administered separately or they can be administered an formulated together. For example, they can be formulated together and administered in conjunction with a separate formulation containing yet another therapeutic agent. While the two or more agents in the combination therapy can be administered simultaneously, they need not be. For example, administration of the conjugate can precede administration of a second agent (or combination of agents) by minutes, hours, days, or weeks. Thus, the two can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. In many cases it is desirable that the conjugate and the second agent be present in within the patient's body at the same time, this need not be so.

The therapeutic conjugate, alone or in combination with a second agent, can be combined with any pharmaceutically acceptable carrier or medium. Thus, the therapeutic conjugate or a combination that includes the conjugate can be combined with materials that do not produce an adverse, allergic or otherwise unwanted reaction when administered to a patient. The carriers or mediums used can include solvents, dispersants, coatings, absorption promoting agents, controlled release agents, and one or more inert excipients (which include starches, polyols, granulating agents, microcrystalline cellulose, diluents, lubricants, binders, disintegrating agents, and the like), etc. If desired, tablet dosages of the disclosed compositions may be coated by standard aqueous or nonaqueous techniques.

Compositions may also optionally include other therapeutic ingredients, anti-caking agents, preservatives, sweetening agents, colorants, flavors, desiccants, plasticizers, dyes, lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The therapeutic conjugates either in their free form or as a salt can be combined with a polymer such as polylactic-glycoloic acid, poly-(I)-lactic-glycolic-tartaric acid (WO 01/12233), polyglycolic acid (U.S. Pat. No. 3,773,919), polylactic acid (U.S. Pat. No. 4,767,628), poly(M-caprolactone) and poly(alkylene oxide) (U.S. 20030068384) to create a sustained release formulation. Such formulations can be used to implants that release the conjugate over a period of a few days, a few weeks or several months depending on the polymer, the particle size of the polymer, and the size of the implant (see, e.g., U.S. Pat. No. 6,620,422). Other sustained release formulations and polymers are described in EP 0 467 389 A2, WO 93/24150, U.S. Pat. No. 5,612,052, WO 97/40085, WO 03/075887, WO 01/01964A2, U.S. Pat. No. 5,922,356, WO 94/155587, WO 02/074247A2, WO 98/25642, U.S. Pat. No. 5,968,895, U.S. Pat. No. 6,180,608, U.S. 20030171296, U.S. 20020176841, U.S. Pat. No. 5,672,659, U.S. Pat. No. 5,893,985, U.S. Pat. No. 5,134,122, U.S. Pat. No. 5,192,741, U.S. Pat. No. 5,192,741, U.S. Pat. No. 4,668,506, U.S. Pat. No. 4,713,244, U.S. Pat. No. 5,445,832 U.S. Pat. No. 4,931,279, U.S. Pat. No. 5,980,945, WO 02/058672, WO 9726015, WO 97/04744, and US20020019446.

The conjugates can be administered, e.g., by intravenous injection, intramuscular injection, subcutaneous injection, intraperitoneal injection, topical, sublingual, intraarticular (in the joints), intradermal, buccal, ophthalmic (including intraocular), intranasaly (including using a cannula), via intracavernosal injection, by transurethral application or by other routes. The agents can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. WO 97/11682) via a liposomal formulation (see, e.g., EP 736299, WO 99/59550 and WO 97/13500), via formulations described in WO 03/094886 or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein. The agents can also be administered transdermally (i.e. via reservoir-type or matrix-type patches, microneedles, thermal portion, hypodermic needles, iontophoresis, electroporation, ultrasound or other forms of sonophoresis, jet injection, or a combination of any of the preceding methods (Prausnitz et al. 2004, Nature Reviews Drug Discovery 3:115-124)). The agents can be administered using high-velocity transdermal particle injection techniques using the hydrogel particle formulation described in U.S. 20020061336. Additional particle formulations are described in WO 00/45792, WO 00/53160, and WO 02/19989. An example of a transdermal formulation containing plaster and the absorption promoter dimethylisosorbide can be found in WO 89/04179. WO 96/11705 provides formulations suitable for transdermal administration. The conjugates can be administered in the form a suppository or by other vaginal or rectal means. The agents can be administered in a transmembrane formulation as described in WO 90/07923. The agents can be administered non-invasively via the dehydrated particles described in U.S. Pat. No. 6,485,706. The agent can be administered in an enteric-coated drug formulation as described in WO 02/49621. The conjugates can be administered intranasally using the formulation described in U.S. Pat. No. 5,179,079. Formulations suitable for parenteral injection are described in WO 00/62759. The agents can be administered using the casein formulation described in U.S. 20030206939 and WO 00/06108. The conjugates can be administered using the particulate formulations described in U.S. 20020034536.

The conjugates described herein and combination therapy agents can be packaged as a kit that includes single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation.

The proper dosage of the therapeutic conjugate can be determined by those skilled in the art. The dosage, for example, can be designed to administer the amount of the therapeutic agent conjugated to the statin that would normally be administered if the therapeutic agent was administered alone. However, the therapeutic conjugate might be administered at a dosage that provides less or far less of the therapeutic agent than would otherwise be administered since the statin is expected to target the therapeutic conjugate to liver cells thereby increasing the effective dose of the therapeutic agent at the liver.

A number of embodiments of the invention have been described. Nevertheless, it will be understood that various modifications may be made without departing from the spirit and scope of the invention. Accordingly, other embodiments are within the scope of the following claims.

The invention claimed is:
1. A compound having the formula:

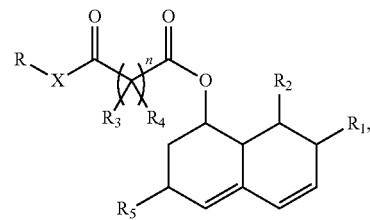

or a pharmaceutically acceptable salt thereof; wherein:
R is a therapeutic agent selected from the group consisting of niacin, diclofenac, etodolac, fenoprofen, floctafenine, flurbiprofen, ibuprofen, indoprofen, indomethacin, ketoprofen, ketorolac, lomoxicam, morazone, naproxen, perisoxal, pirprofen, pranoprofen, suprofen, suxibuzone, tropesin, ximoprofen, zaltoprofen, zileuton, zomepirac, salicylate, bleomycin, capecitabine, carubicin, chlorozotocin, a chromomycin, cladribine, colchicine, cytarabine, daunorubicin, demecolcine, denopterin, docetaxel, doxyifluridine, doxorubicin, dromostanolone, edatrexate, enocitabine, epirubicin, epitiostanol, estramustine, etoposide, floxuridine, fludarabine, formestane, gemcitabine, irinotecan, lentinan, lonidamine, melengestrol, melphalan, menogaril, mitolactol, nogalamycin, nordihydroguaiaretic acid, an olivomycin, paclitaxel, pentostatin, pirarubicin, plicamycin, porfiromycin, prednimustine, puromycin, ranimustine, a ristocetin, temozolamide, teniposide, tomudex, topotecan, tubercidin, ubenimax, valrubicin, vinorelbine, vinblastine, vindesine, vinorelbine, and zorubicin;

n is 1, 2, 3, 4, 5, or 6;

X is S, O or NH;

$R_3$ and $R_4$ are independently selected from the group consisting of —$CH_3$, —OH, H, —$CH_2CH_3$, cyclopropyl, and halogens;

$R_1$ and $R_5$ are independently selected from the group consisting of —$CH_3$ and H; and $R_2$ is selected from the group consisting of:

(a)

(b)

(c)

(d)

2. The compound of claim 1 having the formula:

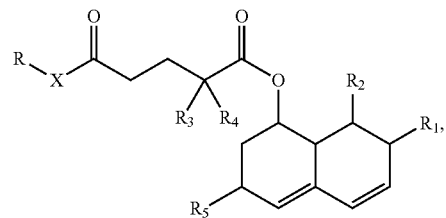

or a pharmaceutically acceptable salt thereof.

3. The compound of claim 1, wherein the compound is of Formula (10a):

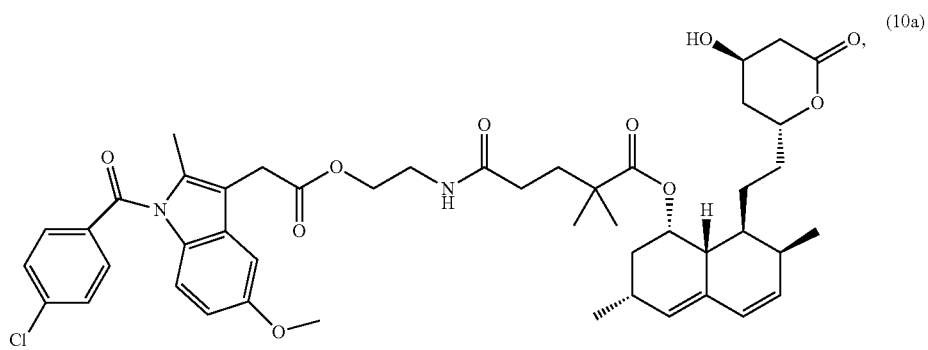 [SMILES: COc1ccc2c(c1)c(CC(=O)OCCNC(=O)CCC(C)(C)C(=O)O[C@H]1C[C@@H](C)C=C3C=C[C@H](C)[C@H](CC[C@@H]4C[C@@H](O)CC(=O)O4)[C@H]31)c(C)n2C(=O)c1ccc(Cl)cc1]

or a pharmaceutically acceptable salt thereof.

4. The compound of claim 1 having the formula:

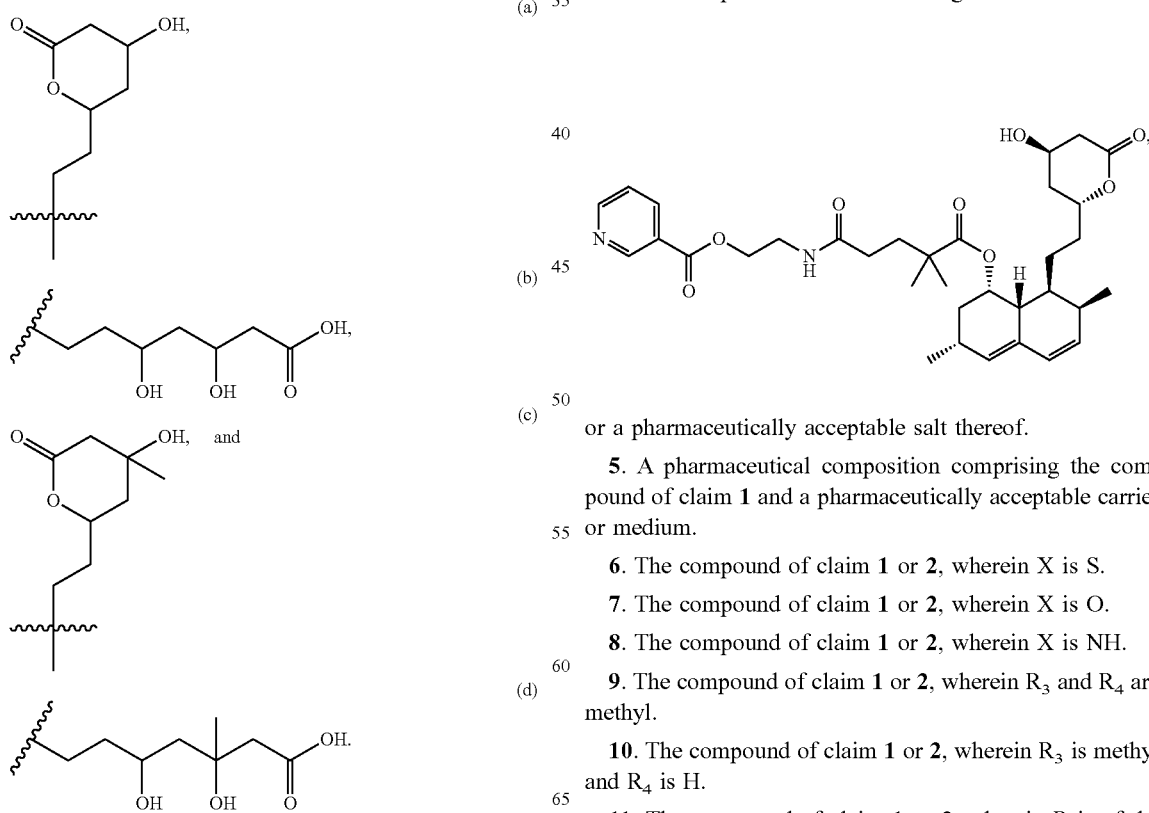

or a pharmaceutically acceptable salt thereof.

5. A pharmaceutical composition comprising the compound of claim 1 and a pharmaceutically acceptable carrier or medium.

6. The compound of claim 1 or 2, wherein X is S.

7. The compound of claim 1 or 2, wherein X is O.

8. The compound of claim 1 or 2, wherein X is NH.

9. The compound of claim 1 or 2, wherein $R_3$ and $R_4$ are methyl.

10. The compound of claim 1 or 2, wherein $R_3$ is methyl and $R_4$ is H.

11. The compound of claim 1 or 2, wherein R is of the formula:

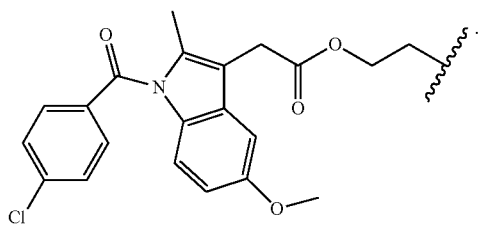 [SMILES: *CCOC(=O)Cc1c(C)n(C(=O)c2ccc(Cl)cc2)c2ccc(OC)cc12]
12. The compound of claim 1 wherein $R_2$ is of the formula:
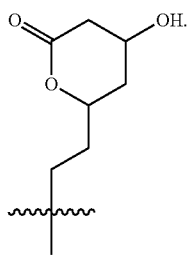 [SMILES: *CCC1CC(O)CC(=O)O1]
13. The compound of claim 1 wherein $R_2$ is of the formula:
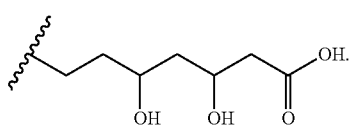 [SMILES: *CCC(O)CC(O)CC(=O)O]
14. The compound of claim 1 wherein $R_2$ is of the formula:
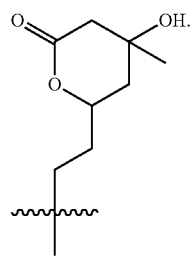 [SMILES: *CCC1CC(C)(O)CC(=O)O1]
15. The compound of claim 1 wherein $R_2$ is of the formula:
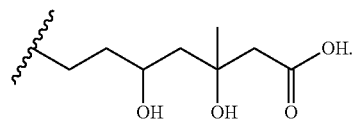 [SMILES: *CCC(O)CC(C)(O)CC(=O)O]
16. The compound of claim 1 having the formula:
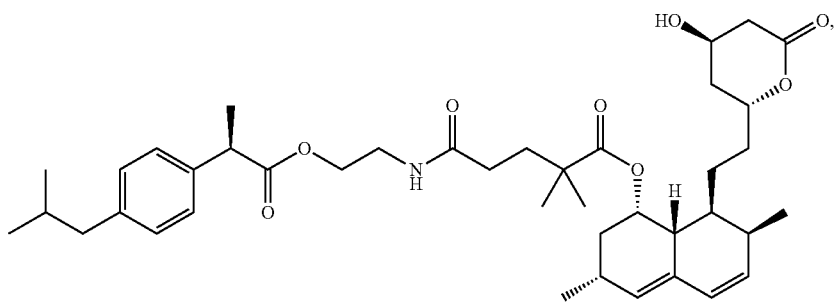 [SMILES: CC(C)Cc1ccc([C@@H](C)C(=O)OCCNC(=O)CCC(C)(C)C(=O)O[C@H]2C[C@@H](C)C=C3C=C[C@H](C)[C@H](CC[C@@H]4C[C@@H](O)CC(=O)O4)[C@H]32)cc1]
or a pharmaceutically acceptable salt thereof.
* * * * *